United States Patent [19]

Stein et al.

[11] Patent Number: 5,968,735
[45] Date of Patent: Oct. 19, 1999

[54] VECTOR FOR THE EXPRESSION OF THERAPY-RELEVANT GENES

[75] Inventors: Ulrike Stein; Wolfgang Walther, both of Berlin, Germany

[73] Assignee: Max Delbruck-Centrum fur Molekular Medizin Berlin, Berlin, Germany

[21] Appl. No.: 08/439,814

[22] Filed: May 12, 1995

[30] Foreign Application Priority Data

Nov. 12, 1992 [DE] Germany ............................ 42 38 778
Nov. 10, 1993 [WO] WIPO ...................... PCT/DE93/01086

[51] Int. Cl.⁶ ............................ C12Q 1/68; C12N 15/85; C12P 21/00
[52] U.S. Cl. .......................... 435/6; 435/69.4; 435/69.5; 435/69.51; 435/69.52; 435/69.6; 435/320.1
[58] Field of Search .......................... 435/6, 7.1, 320.1, 435/172.1, 172.3; 536/23.1, 24.1; 424/93.6; 514/44

[56] References Cited

FOREIGN PATENT DOCUMENTS

WO 89/12109  12/1989  WIPO .

OTHER PUBLICATIONS

"Report and Recommendations of the Panel to Assess the NIH Investment in Research on Gene Therapy", S.H. Orkin and A.G. Arno, Co-chairs, Dec. 1995.

Biedler, J.L., "Genetic Aspects of Multidrug Resistance", *Cancer Supplement*, 70(6):1799–1809 (1992).

Chin, K.–V., et al., "Modulation of Activity of the Promoter of the Human MDR–1 Gene by Ras and p53", *Science* 255:459–462 (1992).

Dittmer, D., et al., "Gain of function mutations in p.53", *Nature Genetics* 4:42–46 (1993).

Ferrandis, E., and Bénard, J., "Activation of the human MDR1 gene promoter in differentiated neuroblasts", *Int. J. Cancer* 54:987–991 (1993).

Hantzopoulos, P.A., et al., "Improved gene expression upon transfer of the adenosine deaminase minigene outside the transcriptional unit of a retroviral vector", *Proc. Natl. Acad. Sci. USA* 86:3519–3523 (1989).

Juranka, P.F., et al., "P–glycoprotein: multidrug–resistance and a superfamily of membrane–associated transport proteins", *The FASEB Journal* 3:2583–2592 (1989).

Kohno, K., et al., "The direct activation of human multidrug resistance gene (MDR1) by anticancer agents", *Biochemical and Biophysical Research Communications* 165(3):1415–1421 (1989).

Kohno, K., et al., "Tissue–specific Enhancer of the Human Multidrug–resistance (MDR1) Gene", *The Journal of Biological Chemistry* 265(32):19690–19696 (1990).

Markowitz, D., et al., "Construction and Use of a Safe and Efficient Amphotropic Packaging Cell Line", *Virology* (167):400–406 (1988).

Miller, A.D., and Buttimore, C., "Redesign of Retrovirus Packaging Cell Lines to Avoid Recombination Leading to Helper Virus Production", *Molecular and Cellular Biology* 6(8):2895–2902 (1986).

Nooter, K., and Herweijer, H., "Multidrug resistance (mdr) genes in human cancer", *Br. J. Cancer* 63:663–669 (1991).

Stein, U., and Walther, W., "Detektion des P–Glycoproteins mit dem Antikörper Anti–P–Glycoprotein 170–180 (Klon JSB–1): Modulation der Multidrug Resistenz in Zytokin–Gen–transfizierten Glioblastomzellen", *Boehringer Mannheim Biochemica Information* 92:22–23 (1994).

Stein, U., et al., "Point Mutations in the mdr1 Promoter of Human Osteosarcomas are Associated With In vitro Responsiveness to Multidrug Resistance Relevant Drugs", *European Journal of Cancer* 30A(10):1541–1545 (1994).

Uchiumi, T., et al., "Involvement of protein kinase in environmental stress–induced activation of human multidrug resistance 1 (MDR1) gene promoter", *FEBS Letters* 326(1, 2,3):11–16 (1993).

Ueda, K., et al., "The Human Multidrug Resistance (mdr1) Gene", *The Journal of Biological Chemistry* 262(2):505–508 (1987).

Ueda, K., et al., "Isolation and Sequence of the Promoter Region of the Human Multidrug–resistance (P–glycoprotein) Gene", *The Journal of Biological Chemistry* 262(36):1732–17436 (1987).

Walther, W., and Stein, U., "Influence of cytokines on mdr1 expression in human colon carcinoma cell lines: increase cytotoxicity of MDR relevant drugs", *J. Cancer Res. Clin. Oncol.* 120:471–478 (1994).

Zastawny, R.L., et al., "The core promoter region of the P–glycoprotein gene is sufficient to confer differential responsiveness to wild–type and mutant p53", *Oncogene* 8:1529–1535 (1993).

Primary Examiner—David Guzo
Attorney, Agent, or Firm—Nikaido, Marmelstein, Murray & Oram LLP

[57] ABSTRACT

A vector for expression of relevant therapeutic genes in mammalian cells which utilizes the mdr promoter, and optionally, the mdr enhancer, operably linked to the therapeutic gene.

9 Claims, 19 Drawing Sheets

Fig.6

INDUCTION OF CAT GENE EXPRESSION BY VINCRISTINE IN MULTIDRUG RESISTENT HCT15 AND SENSITIVE KM12 COLON CARCINOMA CELL LINES, DRIVEN BY WILDTYPE AND POINT MUTATED mdr1 PROMOTER SEQUENCES.

| VINCRISTINE CONCENTRATION | | HCT15 | | | KM12 | | |
|---|---|---|---|---|---|---|---|
| | | pCAT-mdrwt | pCAT-mdr103 | pCAT-mdr137 | pCAT-mdrwt | pCAT-mdr103 | pCAT-mdr137 |
| 0ng/ml | dpm | 378.12 | 495.75 | 451.8 | 176.2 | 343.1 | 287.32 |
| 40ng/ml | dpm | 1155.6 | 1735.13 | 1492.7 | 418.3 | 918.44 | 720.4 |
| | IF | 3.05 | 3.5 | 3.3 | 2.37 | 2.67 | 2.51 |
| 400ng/ml | dpm | 1981.2 | 2837.44 | 2258.31 | 782.15 | 1638.12 | 1288.0 |
| | IF | 5.24 | 5.72 | 5.0 | 4.44 | 4.77 | 4.48 |

IF: INDUCTION FACTOR VINCRISTINE-INDUCED CAT EXPRESSION IN TRANSFECTED CELLS IN RELATION TO THE RESPECTIVE TRANSFECTED, BUT NON-INDUCED CAT EXPRESSION IN CONTROL CELLS.

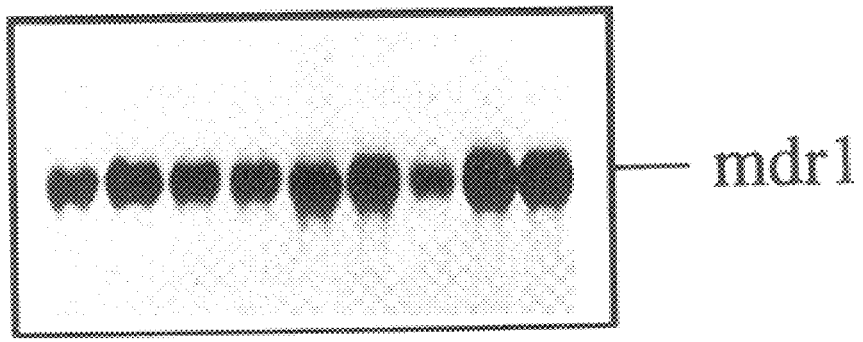
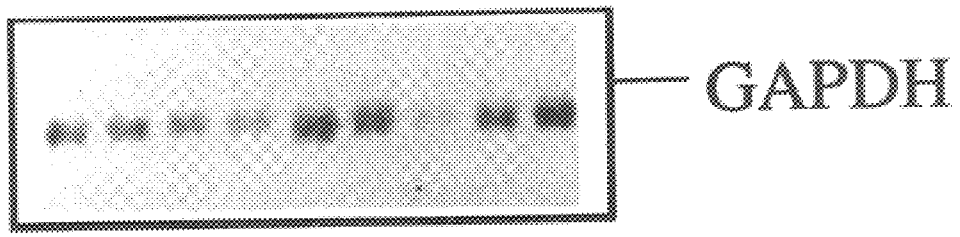
Fig. 7(a)
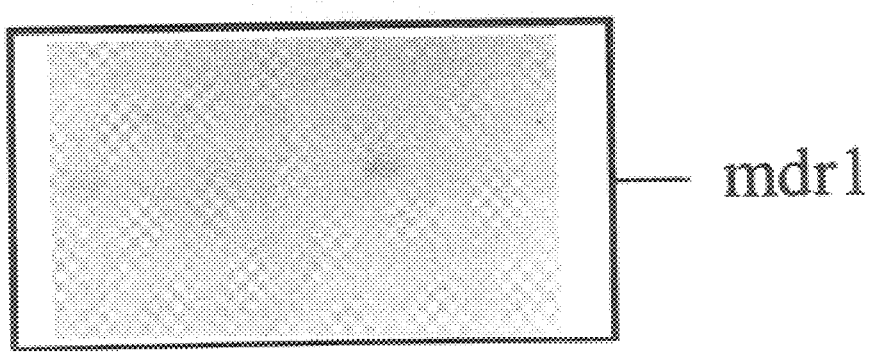
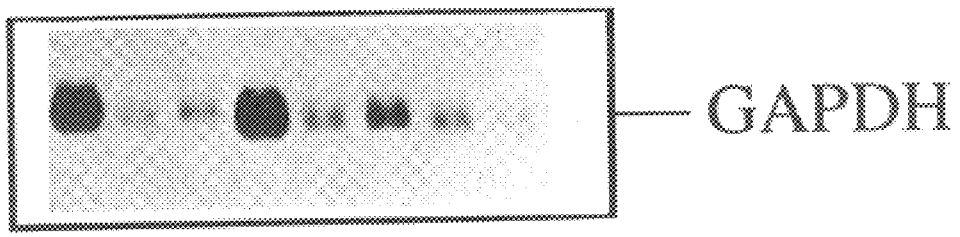
Fig. 7(b)

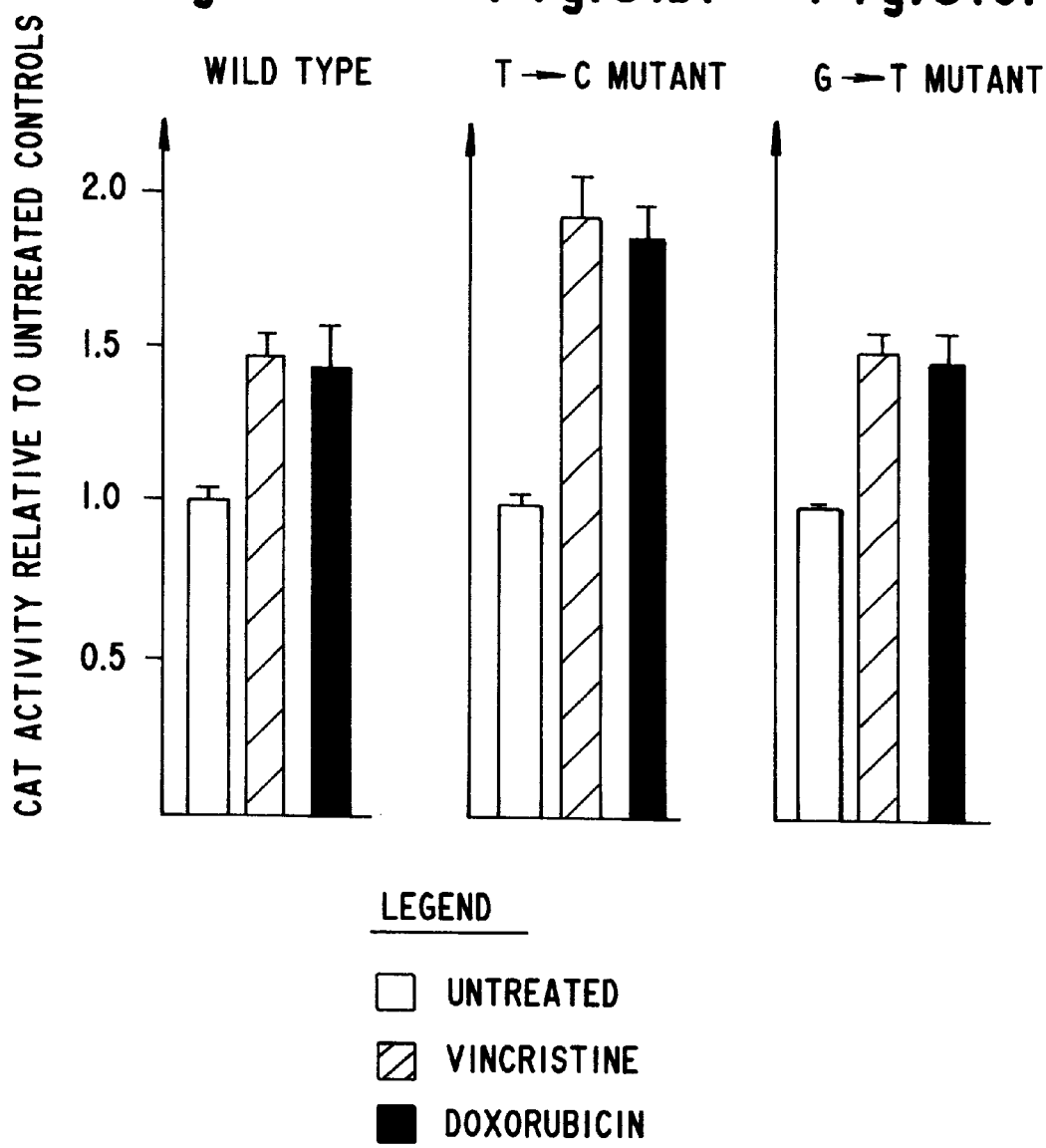

pN2tk-hTNF

Fig.11

PRODUCTION OF BIOLOGICALLY ACTIVE TNFα IN
TRANSFECTED HUMAN U373MG GLIOBLASTOMA CELL CLONES

| CELL CLONES | PRODUCTION OF TNFα IN pg/ml[1] |
|---|---|
| PARENTAL U373MG CELLS | 0 |
| U373-pN2A (EMPTY VECTOR) | 0 |
| U373-pN2tk-hTNF CLONE 1 | 5780 |
| U373-pN2tk-hTNF CLONE 2 | 8200 |
| U373-pN2tk-hTNF CLONE 3 | 7850 |

[1] 5×10⁵ CELLS OF EACH CLONE WERE GROWN FOR 48 HOURS, MEDIUM WAS CHANGED 24 HOURS PRIOR TO SUPERNATANT HARVEST FOR MEASUREMENT IN THE L929 CYTOTOXICITY ASSAY.

Fig.13

RHODAMINE-123 TRANSPORT IN TRANSDUCED HUMAN
U373MG GLIOBLASTOMA CELLS

| CELLS | FLUORESCENCE INTENSITY | | RELATIVE FLUORESCENCE |
| --- | --- | --- | --- |
| (%)[1] | INFLUX[1] | EFFLUX[1] | |
| PARENTAL U373 CELLS | 106 | 15 | 14.1 |
| U373 pN2A | 111 | 19 | 17.1 |
| U373 pN2tk-hTNF1 | 132 | 56 | 42.4 |
| U373 pN2tk-hTNF2 | 174 | 139 | 79.9 |
| U373 pN2tk-hTNF3 | 145 | 86 | 59.3 |

FLUORESCENCE INTENSITY AND RELATIVE FLUORESCENCE ARE BASED ON A CELL
NUMBER OF 1×10$^6$ CELLS AND WERE DETERMINED IN TWO INDEPENDENT EXPERIMENTS.
1 AS DEFINED IN MATERIALS AND METHODS.

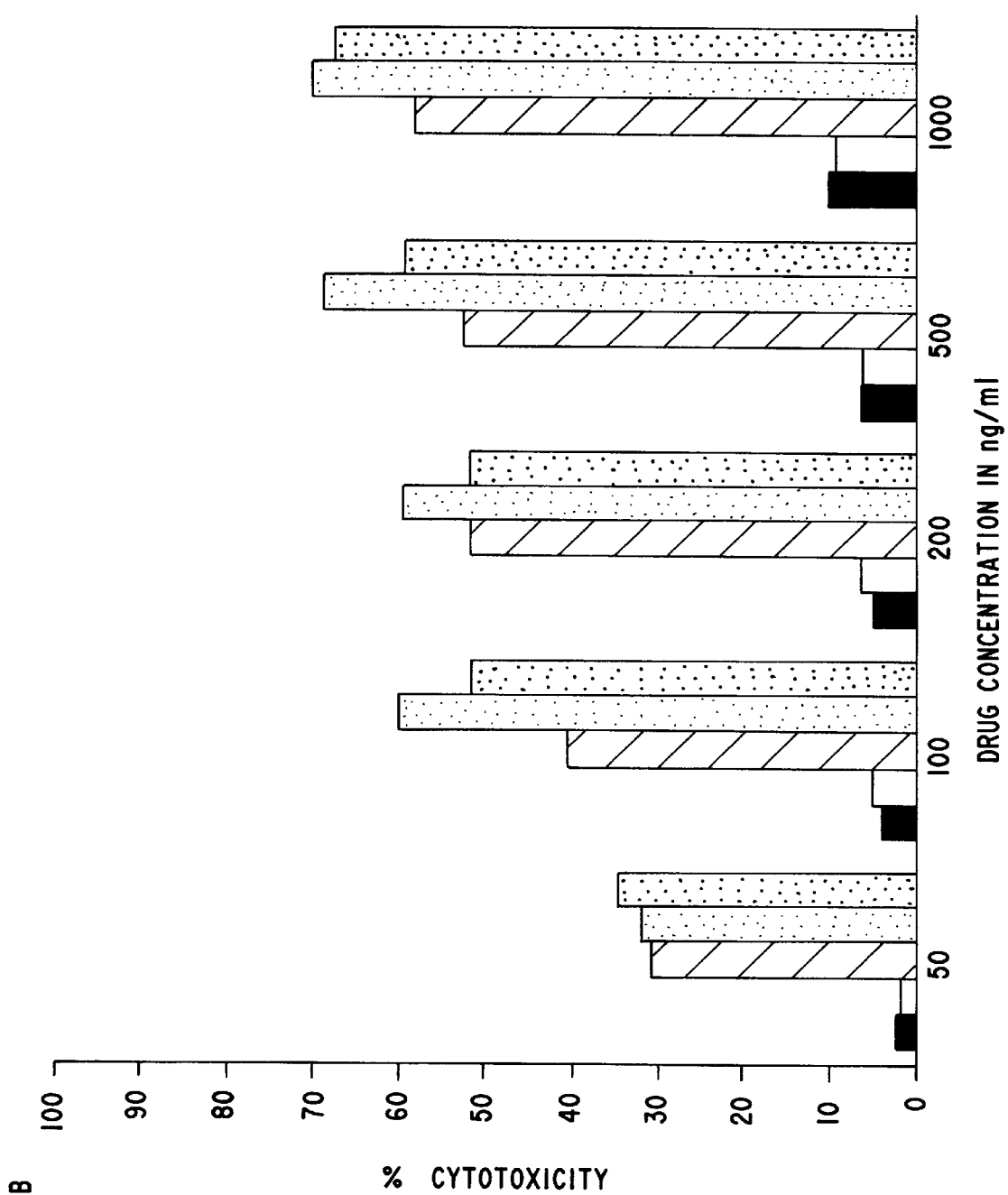

Fig.16

INFLUENCE OF TNFα-SECRETION ON CYTOTOXICITY (IC$_{50}$) OF VINCRISTINE AND DOXORUBICIN IN TRANSDUCED HUMAN U373MG GLIOBLASTOMA CELLS

| CELLS | VINCRISTINE[1] | | DOXORUBICIN[1] | |
|---|---|---|---|---|
| | IC$_{50}$ | DMF[2] | IC$_{50}$ | DMF[2] |
| PARENTAL U373 CELLS | 2.7 | | 3.4 | |
| U373 pN2A | 2.65 | | 3.5 | |
| U373 pN2tk-hTNF1 | 0.1 | 26.5 | 0.2 | 17.5 |
| U373 pN2tk-hTNF2 | 0.09 | 29.4 | 0.095 | 36.8 |
| U373 pN2tk-hTNF3 | 0.095 | 27.9 | 0.2 | 17.5 |

[1] IC$_{50}$ (INHIBITION CONCENTRATION IN µg/ml) WAS DETERMINED BY THE MTT CYTOTOXICITY ASSAY AFTER 3 DAYS INCUBATION OF TUMOUR CELLS WITH VINCRISTINE OR DOXORUBICIN AT 37°C AND IS EXPRESSED AS MEAN VALUE OF THREE EXPERIMENTS.

[2] DMF-DOSE-MODIFYING FACTOR: THE RATIO BETWEEN THE IC$_{50}$ OF CONTROL CELLS AND THE IC$_{50}$ OF TNFα-SECRETING CELLS.

VECTOR FOR THE EXPRESSION OF THERAPY-RELEVANT GENES

CROSS REFERENCE TO RELATED APPLICATIONS

This application is a Continuation-in-Part of PCT International Application No. WO 94/11522.

BACKGROUND OF THE INVENTION

Field of the Invention

The invention relates to a vector and its use for the expression of therapeutically relevant genes in mammal cells. Fields of application of the invention are in the biotechnology industry, the pharmaceutical industry, and in medicine.

In the treatment of cancer patients with cytostatic agents, signs of resistance frequently occur (Igor B. Roninson, 1991), which are an obstacle to achieving the desired therapeutic result. For this reason, a plurality of different chemotherapeutic regimens have been developed, varying the application of the cytostatic agents and their dosage. In addition, attempts were made to enhance chemotherapy by combining cytostatic agents with other groups of substances, such as, e.g., cytokines, monoclonal antibodies, etc. Another way of rendering tumor chemotherapy more effective is the use of antibody-coupled cytostatic agents in order to thereby achieve the transport of the cytostatic agent to the cancer cell and to attain effectiveness in this cell (H. M. Pinedo, et al. 1991). Although partial success has been achieved in some cases, a thorough clinical success could as yet not be achieved with any of these methods.

Successful chemotherapy of human tumors is often limited by simultaneous resistance to structurally and functionally unrelated amphiphilic cytotoxic drugs, the multidrug resistance (MDR) phenotype (Germann, et al, 1993). Classical MDR is mediated by the multidrug resistance gene (mdr1) encoded P-glycoprotein, which acts as an energy-dependent drug-efflux pump (Roninson, 1992). Several studies have demonstrated the inducibility of the mdr1 gene promoter by stress factors, such as differentiating agents, heat shock, arsenite, protein kinase c agonists, as well as by UV irradiation (Mickley et al, 1989; Chin et al, 1990; Chaudhary et al, 1992; Uchiumi et al, 1993; Ferrandis et al, 1993). Modulating effects of MDR associated drugs on the mdr1 promoter have also been reported (Kohno et al, 1989; Licht et al, 1991; Chaudhary et al, 1993; Stein et al, 1994), mostly using the COS monkey kidney system. However, since colon carcinoma cells frequently show high intrinsic mdr1 expression levels, they may represent an important model for investigation of modulated mdr1 expression and the resulting MDR phenotype.

Among human sarcomas, osteosarcomas usually display high intrinsic mdr1 expression while malignant fibrous histiocytomas (MFH) do not. A comparative polymerase chain reaction (PCR)-based sequence analysis of the mdr1 promoter revealed point mutations in 7/9 osteosarcomas at nucleotides +103 (2 cases T→C) and +137 (5 cases G→T). No changes were seen in 8 MFHs. When COS cells transfected with CAT constructs containing the T→C-mutant mdr1 promoters were treated with vincristine or doxorubicin, expression of the chloramphenicol acetyltransferase (CAT) gene was enhanced to a higher extent than with constructs containing wild-type or G→T-mutant mdr1 promoters.

Several investigations have shown that malignant gliomas express P-glycoprotein at high levels. The P-glycoprotein is a product of the multidrug resistance gene (mdr1) and functions as an energy-dependent efflux pump which decreases drug accumulation and cytotoxicity. Since tumor necrosis factor alpha (TNFα) is a powerful anticancer agent used in clinical trials and gene therapy protocols, this cytokine gene was chosen for the present investigations. Transduction of the human TNFα(hTNF) gene carrying retroviral vector pN2tk-hTNF into U373MG human glioblastoma cells resulted in expression and secretion of biologically active hTNF. Release of transduced hTNF reduces P-glycoprotein expression and is associated with enhanced rhodamine-123 uptake and potentiation of cytotoxicity of the MDR relevant drugs vincristine and doxorubicin. Furthermore the transfected cell clones showed a reduced growth rate compared to the parental cells.

Malignancies of the brain including gliomas have poor prognosis due to their aggressiveness and their resistance to radiotherapy and chemotherapy. Several investigations have been made to identify the molecular mechanisms of intrinsic resistance in human and animal brain tumors and tumor models (Mousseau et al., 1993). Among the chemoresistance-related genes the multidrug resistance gene (mdr1) was shown to be involved in reduced response of brain tumors to chemotherapy (Matsumoto et al., 1991). Thus, the overcoming of multidrug resistance provides an attractive goal for a more effective therapy of brain tumors. Beside the occurrence of multidrug resistance (MDR) in patients with malignant gliomas, deficiencies in immunological functions have been observed which may contribute to tumor progression.

Cytokines, including tumor necrosis factor alpha (TNFα), play an important role in immunoregulation and antitumor activities. This fact led to several In Vitro and In Vivo investigations and clinical trials for an immunotherapy of malignant gliomas with TNFα (for review see: Jaeckle, 1994). Tumor necrosis factor is predominantly produced by activated macrophages and can be induced by Natural Killer-(NK), T- and tumor cells (for review see: Tracey and Cerami, 1993). Despite the fact that TNFα is an effective antitumor agent, external TNFα application in glioblastoma patients is surrounded by controversy. New approaches including gene transfer of cytokine genes into glioblastoma cells are being used in an attempt to circumvent the disadvantages of immunotherapy and to potentiate immune response against the tumor (Yu et al., 1993; Sparmann et al., 1994). Furthermore, it has been demonstrated that cytokines are able to modulate mdr1 expression and to enhance cytotoxicity to certain tumor cell lines (Evans and Baker, 1992; Walther and Stein, 1994).

The transfer of the human TNFα (hTNF) gene into U373MG human glioblastoma cells was used to investigate the effects of the cytokine on P-glycoprotein expression and the chemosensitivity to MDR related drugs in stably transfected glioblastoma cells. Introduction of the hTNF-expressing retroviral vector pN2tk-hTNF into U373MG glioblastoma cells revealed that secretion of biologically active hTNF alters growth characteristics, reduces P-glycoprotein expression associated with an enhanced rhodamine-123 uptake and accumulation, and increases cytotoxicity of doxorubicin and vincristine in vitro. This indicates that the endogenous expression of the cytokine is capable of reversing the MDR phenotype and making these cells more susceptible to treatment with MDR relevant drugs, thus providing an alternative approach in the therapy of malignant gliomas.

SUMMARY OF THE INVENTION

The invention uses the mdr expression system for expression of proteins in tumor cells wherein the proteins support tumor therapy.

The compositions and methods of the invention provide a means for a new type of combination therapy, wherein a cytostatic agent which is administered to a cell causes the expression of a heterologous gene linked to the control elements of the mdr1 gene, wherein the heterologous gene has a therapeutic effect, such as cytokine genes or genes for monoclonal antibodies. The object, in particular, is to combine an applied therapeutic agent (cytostatic agent) with a second therapeutic agent (anti-tumorally effective protein), which is formed only within the cancer cells and thus exerts an effect on the cancer cell directly.

The invention makes use of the property of the mdr1 gene that its gene product P-glycoprotein (which is responsible for the type of resistance of multidrug resistance) is inducible by cytostatic agents such as vincristine and adriamycin. This cytostatics-inducible gene expression is mediated via certain promoter and enhancer elements of the mdr1 gene. Surprisingly, it has been found that these promoter and enhancer elements are also capable of expressing other genes, for instance, genes which are of interest in therapy, such as cytokine genes or genes for monoclonal antibodies. The vector according to the invention thus makes possible a cytostatics-induced foreign gene expression in the body cell, and thus a combination of chemotherapy and immunotherapy in situ.

As a basic structure for the vectors according to the invention there are useful all constructs which are suitable for expression in mammalian cells, preferably viral vectors such as adenovirus vectors, most preferably retroviral expression vectors such as N2A, pM3-neo, pM5-neo. The vector constructions are purposefully connected with tumor-specific targeting in a manner known per se, using suitable carrier systems, such as immunoliposomes, retrovirus particles, etc., to provide transport to the target cells in the patient. Packaging or helper cell lines such as PA317 (Miller and Buttimore, 1986), or the cells lines of Markowicz et al, 1988, U.S. Pat. No. 5,278,056 or U.S. Pat. No. 4,861,719) may be used to package the viral particles. The virus particles are then administered to the cells where they are incorporated into the cells and are able then to develop their therapeutic effect. In the tumor cells which have acquired the vectors of the invention, antitumoral substances will be released via the inducible elements, into the cells and into the area surrounding the tumor, as a result of the chemotherapy subsequently administered. Accordingly, by means of the invention chemotherapy can be combined in a new manner with the antitumoral effects of the induced proteins.

The constructs according to the invention function intracellularly. By chemotherapy the expression of the foreign gene is induced by certain cytostatic agents via the MDR promoters/enhancers, which foreign gene can then develop its antitumoral effect directly in situ. In this way, the cytostatic agent and the foreign gene product act on the target cell (tumor cell) simultaneously, and the foreign gene product can, in addition, exert a systemic effect. For cytokines, for instance, this implies that they exhibit, apart from their direct cytotoxic/cytostatic effect on the target cell, also effects on the immune defense of the organism, such as, e.g., activation of T lymphocytes, macrophages, etc, by which they exert a supporting effect in tumor therapy.

By the method of the invention it is possible to introduce in tumor cells, genes which express tumoricidal proteins. The expression of these proteins is induced by drugs which in turn induce the mdr promoter. Such drugs can be, in particular, chemotherapeutic agents and other cytotoxic drugs. Therefore, the invention provides a method for a synergistic combination of chemotherapeutic agents with other agents which are helpful for the destruction of tumor cells. It is especially preferred that the induced gene product should be a protein which is not toxic per se for the cells, but increases its sensitivity against cytotoxic agents. For example, the cytotoxic drugs may induce, via the mdr promoter, the expression of cytokines. Such cytokines down-regulate the mdr expression, causing the tumor cells to be more sensitive to cytotoxic agents.

Although it is preferred that the construct according to the invention is targeted specifically to tumor cells, it is also possible to use constructs without such targeting. This is because the expression of cytokines such as TNFα, IF-γ and IL-2 is not toxic per se for all cells.

The present invention may be practiced with an mdr promoter, including the wild type promoter or the mutated promoters of example 3, or a functional part of any of the above promoters, wherein a functional part of a promoter is a fragment of the promoter which retains the characteristics of the complete promoter such as general ability to promote transcription, and inducibility by cytostatic agents.

The therapeutically relevant proteins of the invention include, but are not limited to, cytokines, enzymes, antibodies, anti-oncogenes, and cytotoxic agents.

A, mdr1-mRNA expression for HCT15 (lane 2) and for KM12 (lane 4) compared to their b-actin-mRNA expression (for HCT15 lane1, for KM12 lane 3) by RT-PCR; B, P-glycoprotein detection in HCT15 and KM12 with the C219 monoclonal antibody by using FACScan analysis; C, P-glycoprotein detection in HCT15 and KM12 with the MRK16 monoclonal antibody by using FACScan analysis; D, adriamycin uptake in HCT15 (1) and KM12 (m), measured by FACScan analysis.

FIG. 4(Parts A–B). Thin layer chromatography (upper level) and liquid scintillation counting (lower level) of the CAT assay from vincristine induced HCT15 cells after transfection with pCAT-mdrwt, pCAT-mdr103 and pCAT-mdr137.

A, vincristine induction (40–500 ng/ml) of pCAT-mdrwt-transfected HCT15, negative control: non-transfected and non-induced HCT15, positive control: pSV2CAT-transfected HCT15;

B, vincristine induction (40 and 400 ng/ml) of pCAT-mdrwt-▒, pCAT-mdr103-▧ or pCAT-mdr137-▣ transfected HCT15, negative control: non-transfected and non-induced HCT15.

FIG. 5(Parts A–B). Thin layer chromatography (upper level) and liquid scintillation counting (lower level) of the CAT assay from vincristine induced KM12 cells after transfection with pCAT-mdrwt, pCAT-mdr103 and pCAT-mdr137. A, vincristine induction (40–500 ng/ml) of pCAT-mdrwt-transfected KM12, negative control: non-transfected and non-induced KM12, positive control: pSV2CAT-transfected KM12; B, vincristine induction (40 and 400 ng/ml) of pCAT-mdrwt-▒, pCAT-mdr103-▧ or pCAT-mdr137-▣ transfected KM12, negative control: non-transfected and non-induced KM12.

FIG. 6. Induction of CAT gene expression by vincristine in multidrug resistant HCT 15 and sensitive KM12 colon carcinoma cell lines, driven by wildtype and point mutated mdr promoter sequences.

FIG. 7(Parts A–B). mdr expression in human bone and soft tissue sarcomas.

FIG. 8(Parts A–C). Effects of vincristine and doxorubicin on CAT expression in transfected COS cells.

Figure 9:
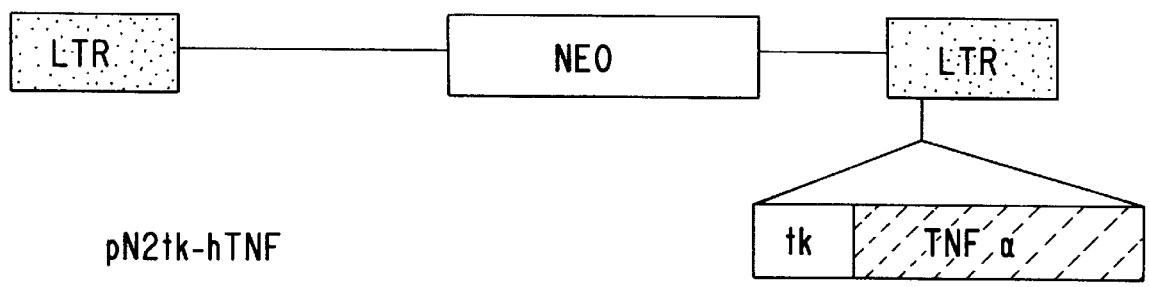

FIG. 9. Vector pN2tk-hTNF

Figure 10:
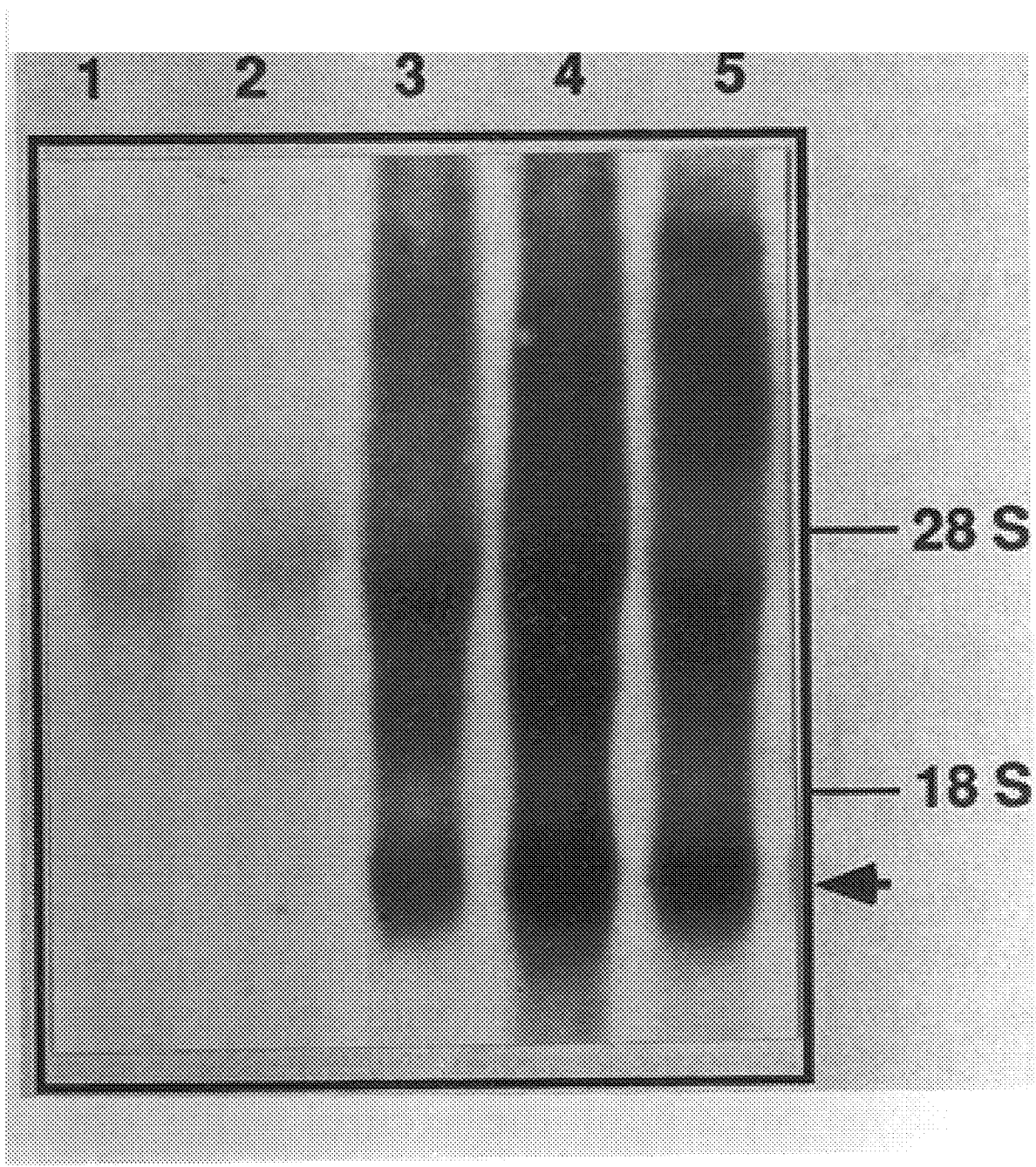

FIG. 10. Northern blot analysis of transduced hTNF-expression U373MG clones.

FIG. 11. Production of biologically active TNFα in transfected glioblastoma cell lines FIG. 12. Influence of hTNF secretion on growth of transfected U373MG glioblastoma cells.

FIG. 13. Rhodamine-123 transport in transduced human U373MG glioblastoma cells.

Figure 14:
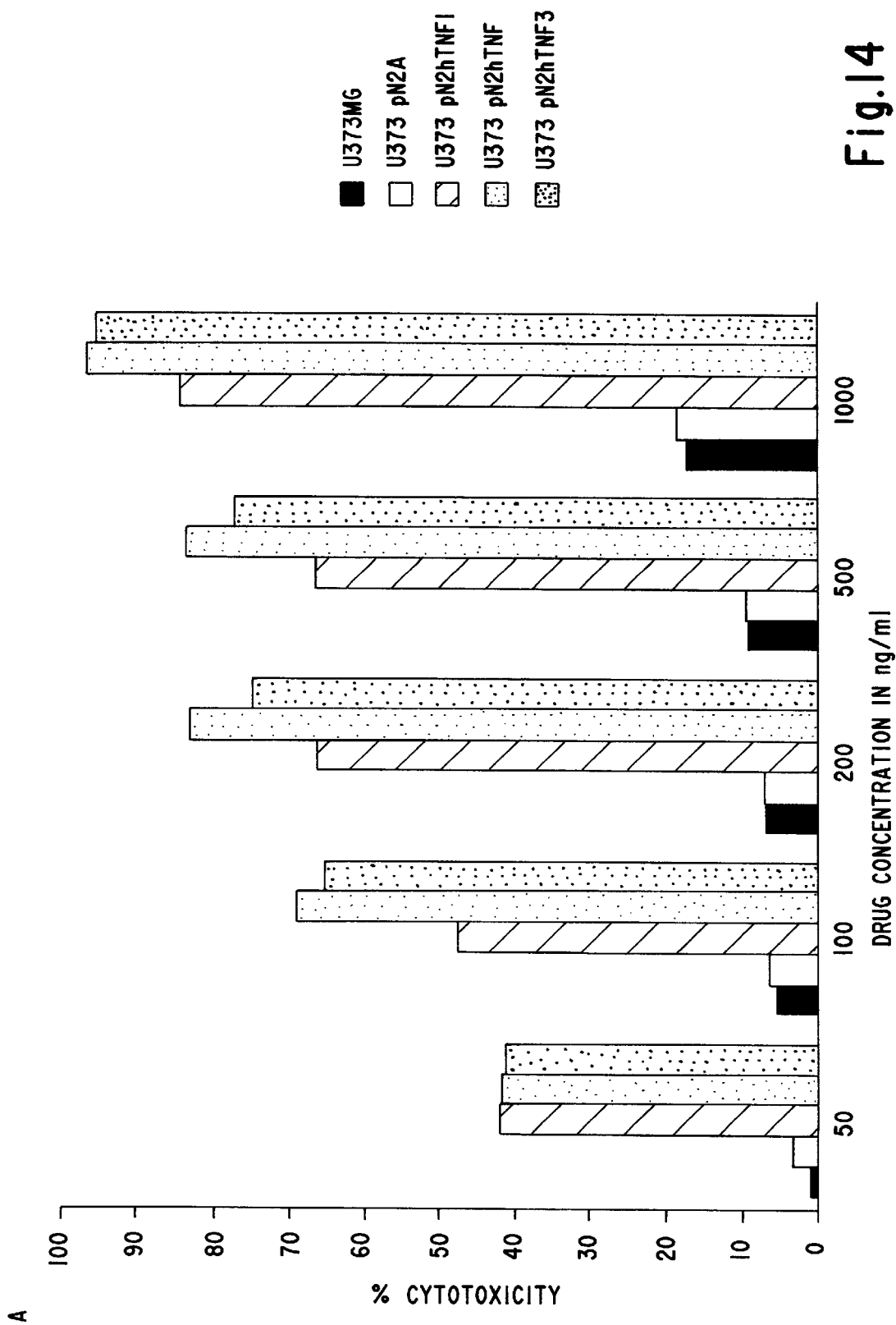

FIG. 14. Effect of hTNF secretion on drug cytotoxicity in transfected cells.

FIG. 15. Effect of hTNF secretion on drug cytotoxicity in transfected cells.

FIG. 16. Influence of TNF-α secretion on cytotoxicity of vincristine and doxorubicin.

The invention shall be illustrated more fully hereinafter by the following non-limiting examples.

DESCRIPTION OF THE PREFERRED EMBODIMENTS

EXAMPLE 1

Construction of a Vector CVS-SW1 for the Cytostatics-inducible Expression of a Therapeutically Relevant Gene Polymerase Chain Reaction (PCR)

High weight molecular human DNA is isolated in a manner known per se from in vitro cell lines or tumor material. Then the promoter sequences of the mdr1 gene and the enhancer sequences of the mdr1 gene, are amplified by PCR (1 min 94° C.; 1 min 45° C.; 2 min 72° C.; 30 cycles) (Kohno et al. J. Biol. Chem. 265: 19690–19696, 1990).

In the case of this construction example, to carry out the PCR of the mdr1 promoter sequences, primers are used (17 bases of the 5'- and 3'-mdr1 promoter sequence+bases of the respective restriction endonucleases+protective group TAC), at the 5' end of which specific sequences for Apa I cloning (GGGCCC), and at the 3' end of which sequences for Sma I (CCCGGG)- and Bgl II (AGATCT) cloning, are located.

Amplification of the enhancer sequence of the mdr1 gene is carried out with 5'-Sst II (CCGCCG)- and Sma I (CCCGGG) primers and 3'-Mlu I (ACGCG) primers (again 17 bases of the 5'- and 3'-mdr1 enhancer sequence+bases of the respective restriction endonucleases+protective group TAC).

Then, the resultant amplificates of the mdr1 promoter and enhancer sequences are cleaved with Apa I/Bgl II and with Sst II/Mlu I respectively, are purified and, thus, are available for cloning into the vector N2A.

Cloning

The retroviral "double copy" vector N2A (Hantzopoulos et al., 1989) having a size of 9,678 kb is first cleaved with Apa I/Bgl II and ligated with amplificates of a mdr1 promoter sequence of SEQUENCE ID No. 1. This intermediate construct I is transformed into suitable bacteria and isolated by the method of plasmid amplification in a known manner from 500 ml of a bacterial suspension ($OD_{600}$=0.4). The purification of the plasmid DNA is carried out by known methods such as CsCl gradient centrifugation. By carrying out another restrictase cleavage with Apa I and Bgl II, the plasmid DNA is obtained with the respective promoter fragment. (All cloning procedures are confirmed with agarose gel electrophoresis.)

This intermediate construct I (vector N2A with a cytostatics-inducible mdr1 promoter sequence) is now cleaved with the restrictases Sst II and Mlu I to ligate the mdr1 enhancer sequence (5'-Sst II; 3' Mlu I) with the intermediate construct I. The intermediate construct II then obtained is again transformed into bacteria and grown on the scale of a 500 ml bacteria culture, and isolated.

Figure 1:
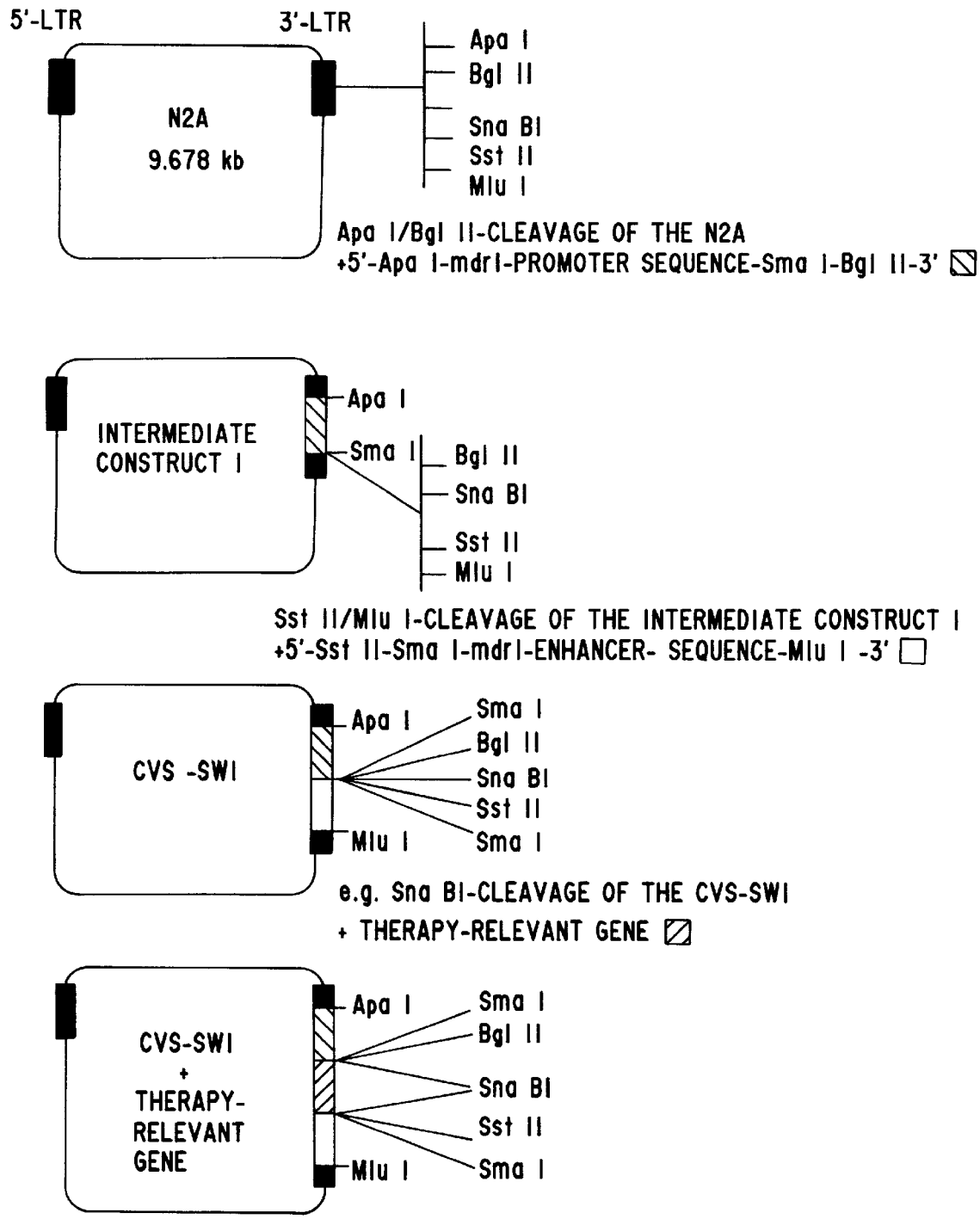
FIG. 1. Retroviral vector CVS-SW1.

Thus there is provided, as a gene-therapeutic principle, a cassette vector system CVS-SW1 for the cloning (e.g., at the SMA I site or Sna BI site) of foreign genes, which are of therapeutic interest, such as, e.g., cytokines, monoclonal antibodies or anti-oncogenes, for the cytostatics-inducible in situ expression thereof (FIG. 1).

Induction of a Foreign Gene in the Cassette Vector System CVS-SW1

The inducibility of a foreign gene in the cassette vector system CVS-SW1 is examined using as an example the CAT gene (chloramphenicolacetyltransferase) after transfection of the construct CVS-SW1 with the CAT gene in COS cells by means of CAT-ELISA (enzyme immunoassay for quantitative determination of chloramphenicolacetyltransferase in transfected, eukaryotic cells).

The testing of the inducibility of a therapeutically relevant gene may be carried out by expression analyses at the RNA and protein levels, and/or by testing the biological activity of the properties and function of the foreign gene product.

Liposomal encapsulation and application of the constructs

The encapsulation of the cytostatics-inducible cassette vector systems (e.g. CVS-SW1) with a therapeutically relevant gene, the tissue- and tumor-specific targeting by means of the liposomes, and the introduction in in vitro cell cultures as well as in in vivo systems (nude mouse) are accomplished by standard methods such as those disclosed in (Nicolau et al. 1989) and (Hug et al, 1991).

Application in cancer patients is guided by various studies in the prior art (Miller, 1992; Culver et al., 1992; Ram, 1993).

Transduction into a Packaging Cell Line

The packaging of the cytostatics-inducible cassette vector systems with a therapeutically relevant gene is accomplished by transduction of the constructs into a packaging cell line. A cell line particularly suitable for this purpose is the packaging line PA 317.

EXAMPLE 2

Construction of a Vector CVS-SW2 for the Cytostatics-inducible Expression of a Therapeutically Relevant Gene In a similar manner, but with correspondingly changed cloning sites, the cloning of the cassette vector system CVS-SW2, comprising the following series: 1. mdr1 enhancer sequence, 2. mdr1 promoter sequence, and 3. the gene which is of therapeutic interest.

EXAMPLE 3

Figure 2:
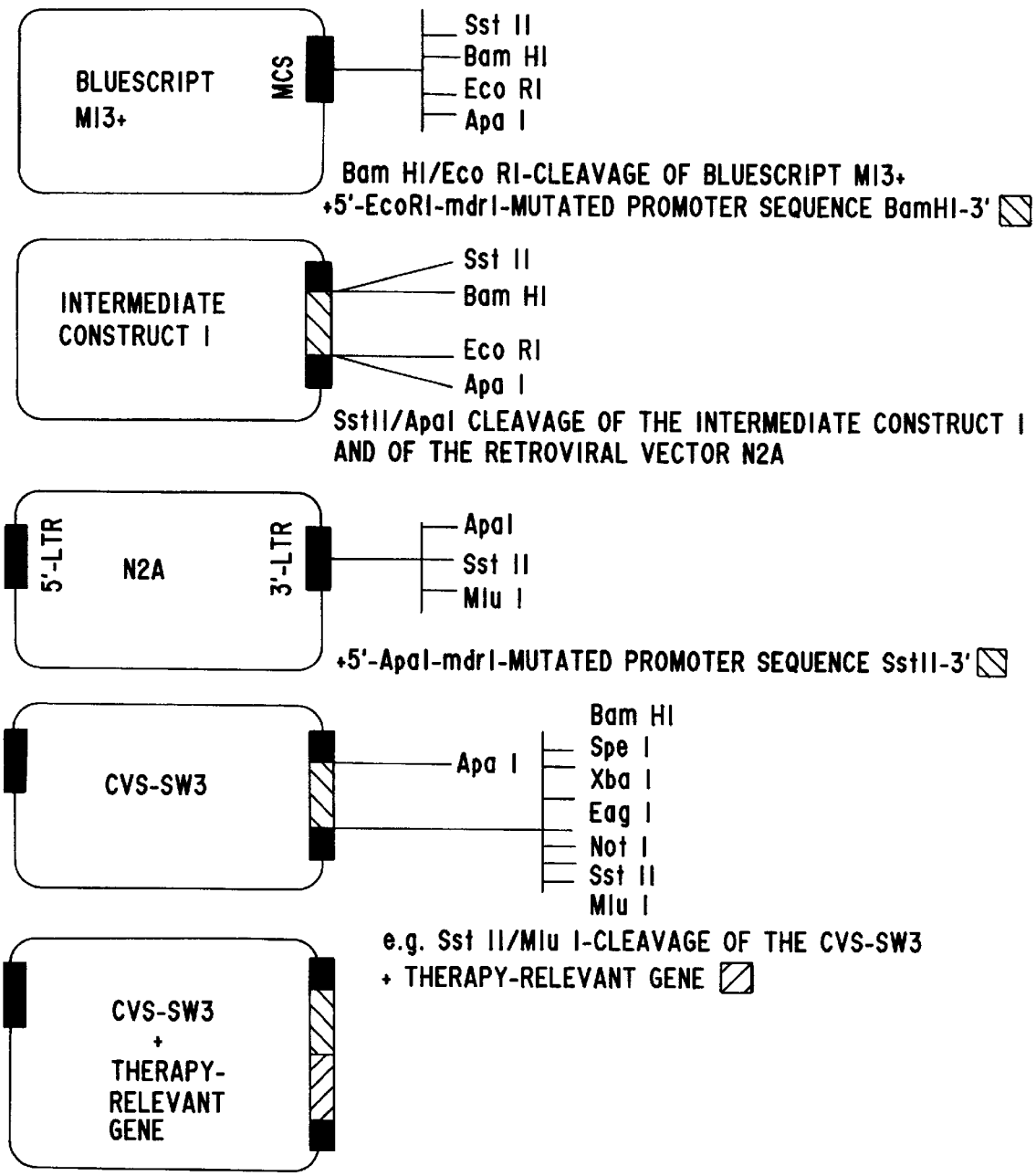
FIG. 2. Retroviral vectors CVS-SW3 and CVS-SW4.

Construction of the Vectors CVS-SW3 and CVS-SW4 for the Cytostatics-inducible Expression of Therapeutically Relevant Genes The cloning of the cassette vector systems CVS-SW3 and 4 is carried out in a manner similar to the one described in Examples 1 and 2 but with correspondingly changed cloning sites and with previous cloning in the vector bluescript M13+. The mutated mdr1 promoter sequences of claim 3a) and b) are involved here. For the cloning of the therapeutically relevant gene into the vectors CVS-SW3 and CVS-SW4 respectively, apart from the cleavage sites mentioned in Examples 3 and 4, also the sites Bam HI, Spe I, Xba I, Eag I and Not I are available (FIG. 2).

In an analogous manner, other eukaryotic expression vectors, can be utilized for foreign gene expression inducible by cytostatic agents. This involves the further steps of introduction of a foreign gene into the cassette vector systems CVS-SW2, 3 and 4, of liposomal encapsulation of the construct, and of its transduction into a packaging cell line, and application.

EXAMPLE 4

Multidrug Resistance Gene (mdr1) Promoter Efficacy and Drug-inducibility in Cells with Different MDR Phenotypes Multidrug resistant HCT15 and drug sensitive KM12 human colon carcinoma cell lines were transfected with constructs incorporating the CAT reporter gene, driven by wildtype and point mutated mdr1 promoter regions. The basal CAT-expression level in HCT15 cells was markedly elevated compared to KM12 cells. CAT-induction by vincristine was dose-dependent over a broad concentration range (40–500 ng/ml) in both lines. However, the induction levels were related to the cells' MDR phenotype with the HCT15 cells showing the greater effect. In both cell types, basal and drug-induced CAT-expression were significantly enhanced by the point mutated promoter regions.

Effects of exogenous agents such as sodium butyrate and P-glycoprotein antagonists on mdr1 expression in colon carcinoma cells have previously been demonstrated (Frommel et al, 1993; Herzog et al, 1993). Their MDR characteristics were defined at the mdr1-mRNA level by reverse transcriptase-polymerase chain reaction (RT-PCR), at the P-glycoprotein expression level using monoclonal antibodies MRK16 and C219 and FACScan analysis and at the P-glycoprotein functional level by adriamycin uptake, also performed by FACScan analysis. Both cell lines were transfected with pCAT-Basic plasmids carrying the reporter gene chloramphenicol acetyltransferase (CAT) driven by the wildtype or two different point mutated-mdr1 promoter sequences. The use of mutated promoter sequences, PCR-amplified originally from human tumor specimen as described earlier (Stein et al, 1993), provided the opportunity to determine the influence of these mutations on drug inducibility in cells with dramatically different intrinsic mdr1 expression. Transfected cells were treated with a wide concentration range of vincristine (40–500 ng/ml) and CAT expression was analyzed by CAT assay using thin layer chromatography (TLC) as well as liquid scintillation counting (LSC).

Cell Lines

The human colon carcinoma cell lines KM12 (Morikawa et al, 1988) and HCT15 (16) were grown in RPMI 1640 medium supplemented with 10% fetal calf serum (Hy Clone, Logan, Utah) and 5 mM L-glutamine at 37° C. and 5% $CO_2$.

Determination of mdr1 Expression by RT-PCR

Total cellular RNA was isolated by using the RNA-miniprep technique (Walther et al, 1994). RT-PCR was performed with the Gene Amp RNA PCR Kit (Perkin Elmer via Roche Molecular Systems Inc., Branchburg, N.J.). The RT reaction was carried out by using the random hexamer primers supplied with the kit and 1 mg of each miniprep RNA. The PCR was performed using mdr1 specific primers (Noonan et al, 1990) producing a 167 bp product, or β-actin specific primers (Wu et al, 1992) producing a 316 bp product. Reverse transcription reaction was performed at 42° C. for 15 min, followed by a denaturation step at 99° C. for 5 min and a cooling step at 5° C. for 5 min. Amplification was started at 95° C. for 2 min, continued for 35 cycles of melting (at 95° C. for 1 min) and annealing-extending (at 60° C. for 1 min), followed by a final step at 72° C. for 7 min. RT-PCR products were separated in an 1.5% agarose gel and quantitated by densitometry using the Image program 1.37.

P-glycoprotein Detection by C219 and MRK16 Immuno Flow Cytometry.

HCT15 and KM12 cells were trypsinized and harvested in phosphate buffered saline (PBS; w/o $Ca^{2+}$ and $Mg^{2+}$). For the detection of P-glycoprotein by the monoclonal antibody C219 (Signet Laboratories Inc., Dedham, Mass.) which recognizes an intracytoplasmic epitope, cells were permeabilized by incubation in 3.7% formaldehyde for 10 min at RT and washed once with PBS. All cells were resuspended in 2% heat inactivated human AB serum (Irvine Scientific, Santa Ana, Calif.) for 5 min at room temperature to prevent non-specific antibody binding. Cells were washed once and incubated at 4° C. with the appropriate monoclonal antibody in a PBS solution containing 2% bovine serum albumin: 2 mg of C219/5×$10^5$ cells for 60 min, or in a 1:100 dilution of MRK16 (Hoechst Japan Ltd., Japan) which recognizes an external epitope of P-glycoprotein, for 30 min. Cells incubated with the Mouse $IgG_1$ (Becton Dickinson Immunocytometry Systems, San Jose, Calif.) served as negative controls. After washing with PBS, cells were treated with a fluorescein-conjugated goat-anti-mouse antibody (TAGO Inc., Burlingham, Calif.) for 30 min at 4° C. After washing, their fluorescence intensity was measured with a FACScan flow cytometer (Becton Dickinson, Mountain View, Calif.).

Adriamycin-Uptake-Assay.

The time-dependent uptake of the fluorescent anthracycline adriamycin (Sigma, St. Louis, Mo.) was measured as a functional index of P-glycoprotein activity. Cells were trypsinized and washed with RPMI 1640/5% FCS, aliquoted and incubated at 37° C. in RPMI 1640/5%FCS containing 50 mM adriamycin for 30 min, 1, 2, 3 or 5 h, respectively. Cells were washed twice with medium and fluorescence intensity was determined by flow cytometry using the FACScan.

PCR-amplification of mdr1 promoter sequences and construction of pCAT-constructs.

The mdr1 promoter sequences (−207 to +158) were amplified from high molecular weight DNA of human osteosarcoma tumor specimen using mdr1 specific primers as described previously (Stein et al, 1994; Stein et al, 1993) and cloned into the BamHI/EcoRI sites of the pBluescriptII SK+/−plasmid (Stratagene, La Jolla, Calif.). For cloning of the mdr1 promoter sequences into pCAT-Basic-vector (Promega, Madison, Wis.) the fragments were taken from pBluescript-constructs by HindIII/SpeI digestion and inserted into the HindIII and SpeI-compatible XbaI sites of pCAT-Basic, creating pCAT-mdrwt (harboring the wild type promoter sequence), pCAT-mdr103 (harboring the T→C-mutated promoter sequence at position +103) and pCAT-mdr137 (harboring the G→T-mutated promoter sequence at position +137).

Electroporation of KM12 and HCT15 Cells and Induction by Vincristine.

Transfer of the pCAT-constructs was performed by electroporation. Exponentially growing KM12 and HCT15 cells were harvested by trypsinization, centrifuged at 800 rpm/min for 5 min at 4° C. and cell pellets were resuspended in ice cold PBS by adjusting the cell concentration to $5 \times 10^5$ cells/ml. 0.8 ml of the cell suspensions were aliquoted into electroporation cuvettes (Invitrogen, San Diego, Calif.), 20 mg plasmid DNA of pCAT-mdrwt, pCAT-mdr103, pCAT-mdr137 and pSV2CAT (served as positive control), respectively, were added and cells were kept on ice for 10 min. Electroporation was done at 1000 mF, 300 V in the Electroporator II apparatus (Invitrogen, San Diego, Calif.), thereafter cells were kept on ice for another 10 min and then seeded in cell culture flasks (Nalgene, Rochester, N.Y.). Cells were grown for 48 h and treated with vincristine at several concentrations (40, 50, 100, 200, 300, 400, and 500 ng/ml) for 24 h, before being harvested for the CAT-assay. CAT-assay, TLC and LSC.

To determine the mdr1 promoter efficacy (wildtype vs. mutated promoter sequences) and their inducibility by MDR associated drugs the CAT-assay was performed by TLC and LSC. The assay was carried out with a commercially available kit (CAT enzyme assay system; Promega, Madison, Wis.) and [$^{14}$C]labeled chloramphenicol (0.05 mCi/ml; NEN Du Pont, Boston, Mass.). Cell lysis was done using the freeze/thaw protocol in accordance with the recommendations of the manufacturer. Protein determination of the cell extracts was performed using the Coomassie Plus Protein Assay Reagent (Pierce, Rockford, Ill.) and the protein concentration was adjusted to 50 mg/125 ml.

Samples were incubated for 3 h at 37° C. and after a brief spin divided for TLC (100 ml) and LSC (25 ml). Reaction was stopped by adding 400 ml ethyl acetate to the TLC-samples and 60 ml xylene to the LSC-samples. TLC was carried out on Silica Gel plates (Analtech Inc., Newark, Del.) and quantitated with a Phospho Imager SF (Molecular Dynamics, Sunnyvale, Calif.). Measurement of the LSC-samples was performed using a LS 6000 LL apparatus (Beckman Instruments, Palo Alto, Calif.).

Statistical Analysis.

The levels of statistical significance were evaluated with data from at least three independent CAT-assays using Student's t-test.

MDR Characteristics of the Colon Carcinoma Cell Lines HCT15 and KM12.

Figure 3A:
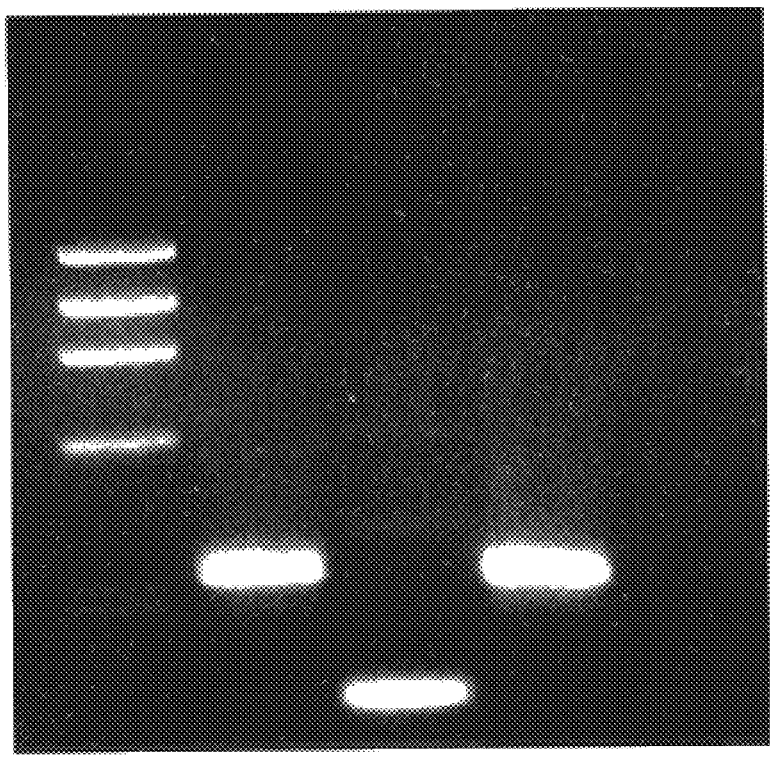
FIG. 3(Parts A–D). Comparison of the colon carcinoma cell lines HCT15 and KM12 with respect to their MDR characteristics.

To evaluate the efficacy and inducibility of the mdr1 promoter in the context of different MDR phenotypes, the human colon carcinoma cell lines HCT15 and KM12 were characterized according to mdr1 expression and P-glycoprotein function. Both cell lines were compared in their mdr1-mRNA expression by RT-PCR, obtaining mdr1 specific 167 bp-RT-PCR-products (FIG. 3A). Quantitative analysis by using the Image 1.37 program revealed that the mdr1 mRNA-expression in the multidrug resistant cell line HCT15 was more than 6 times higher compared to the sensitive KM12 cells. The results were verified by β-actin-specific RT-PCRs, carried out under the same conditions.

Figure 3B:
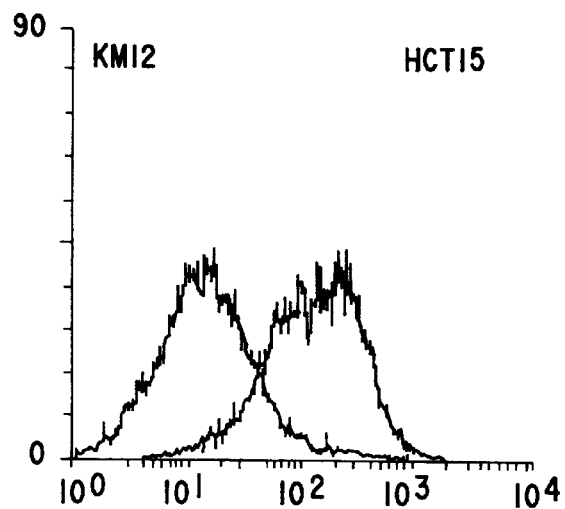
Figure 3C:
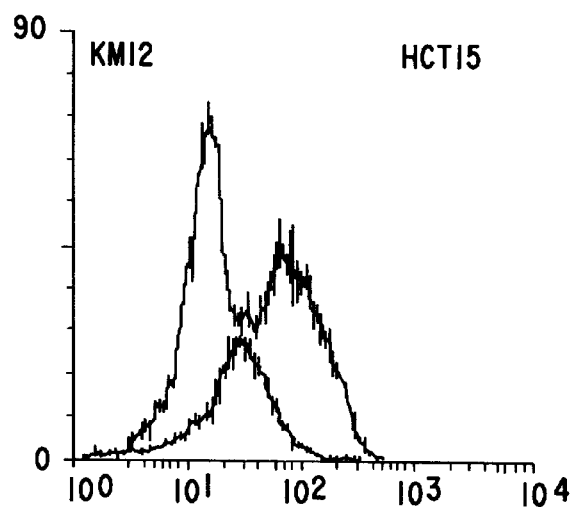
Figure 3D:
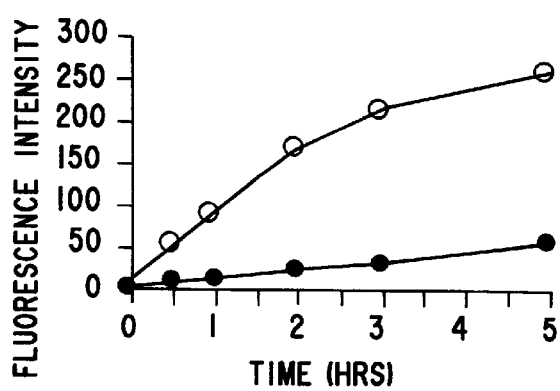

Determination of P-glycoprotein expression was performed using the two monoclonal antibodies MRK16 and C219 by FACScan measurements. FACScan histograms for MRK16 showed a mean fluorescence per cell of 186.11 for HCT15 and 29.37 for KM12, depicted in FIG. 3B. Therefore, the MRK16-detected P-glycoprotein expression in the resistant HCT15 cells was approximately 6 times higher than in the sensitive KM12 cells. Results obtained with the C219 antibody demonstrated a similar situation (FIG. 3C): on average, the mean fluorescence per cell for HCT15 was 82.42, whereas the average value for KM12 was 21.99, reflecting a 4 fold higher P-glycoprotein expression level for HCT15 compared to KM12.

To assess mdr1 expression on functional level, the uptake of the fluorescent MDR associated drug adriamycin was measured and quantitated by FAcscan analysis in both lines. Time dependent adriamycin uptake was approximately 5 times higher in the drug sensitive cell line KM12 compared to the multidrug resistant HCT15 cells, shown in FIG. 1D. This is reflected by mean fluorescences of 257.80 for KM12 and 54.81 for HCT15, measured after 5 h incubation.

The data obtained for mdr1 expression on RNA and protein level as well as P-glycoprotein function correspond well to the MDR phenotype of these cell lines and are in agreement with previous findings (Wu et al, 1992). They firmly establish the MDR phenotype of these cells and their suitability for use in analysis of drug-induced CAT reporter gene expression in multidrug-resistant and sensitive cells.

Basal CAT Expression Driven by Wild Type mdr1 Promoter in HCT15 and KM12 Cells.

Analysis of the non-induced wild type mdr1 promoter in cells with different mdr1-expression, P-glycoprotein function and MDR phenotype should help to reveal its basic function. The pCAT-mdrwt construct, harboring the wild type mdr1 promoter sequence, was transfected into HCT15 and KM12 and the average basal CAT gene expression levels were determined 72 h post transfection. The values of non-induced cells, shown in FIG. 4A for HCT15 and FIG. 5A for KM12, are different. On average, the basal CAT gene expression in the transfected and non-induced resistant HCT15 cells is more than 2 fold higher than in the sensitive KM12 cells. This significant elevation ($P<0.006$) in basal mdr1 promoter activity is consistent with the MDR phenotype of these cells. The significance of this observation is supported by the fact that CAT expression in the pSV2CAT-transfected cells (served as positive controls) was comparable in both lines (FIG. 4A and 5A), regardless of their MDR characteristics ($P>0.05$).

Dose-dependent Vincristine-induced CAT Expression, Driven by Wildtype mdr1 Promoter.

Figure 4A:
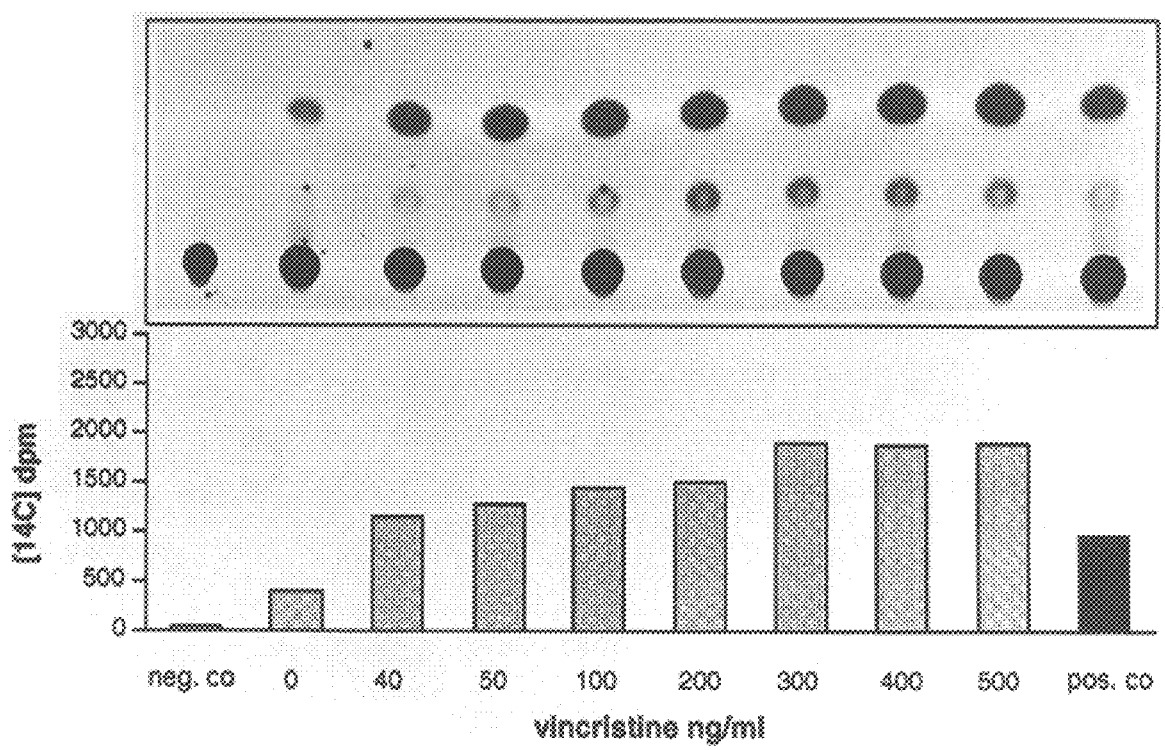
Figure 4B:
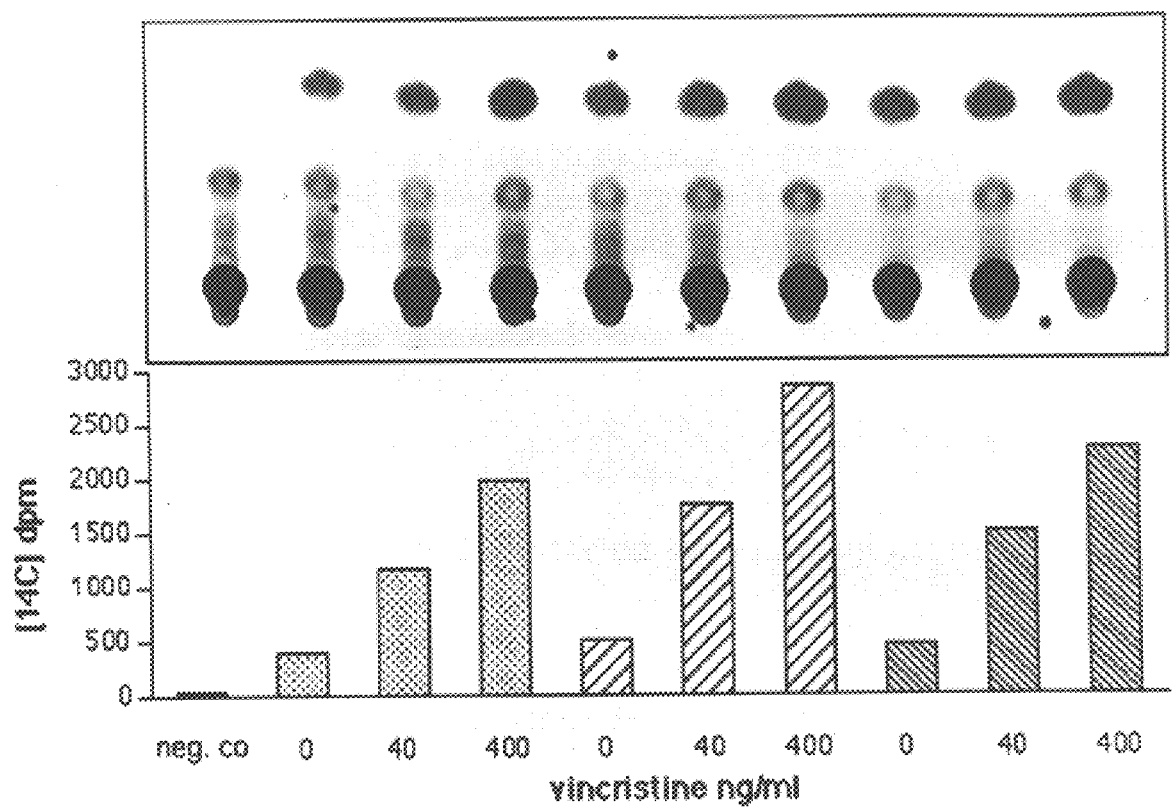
Figure 5A:
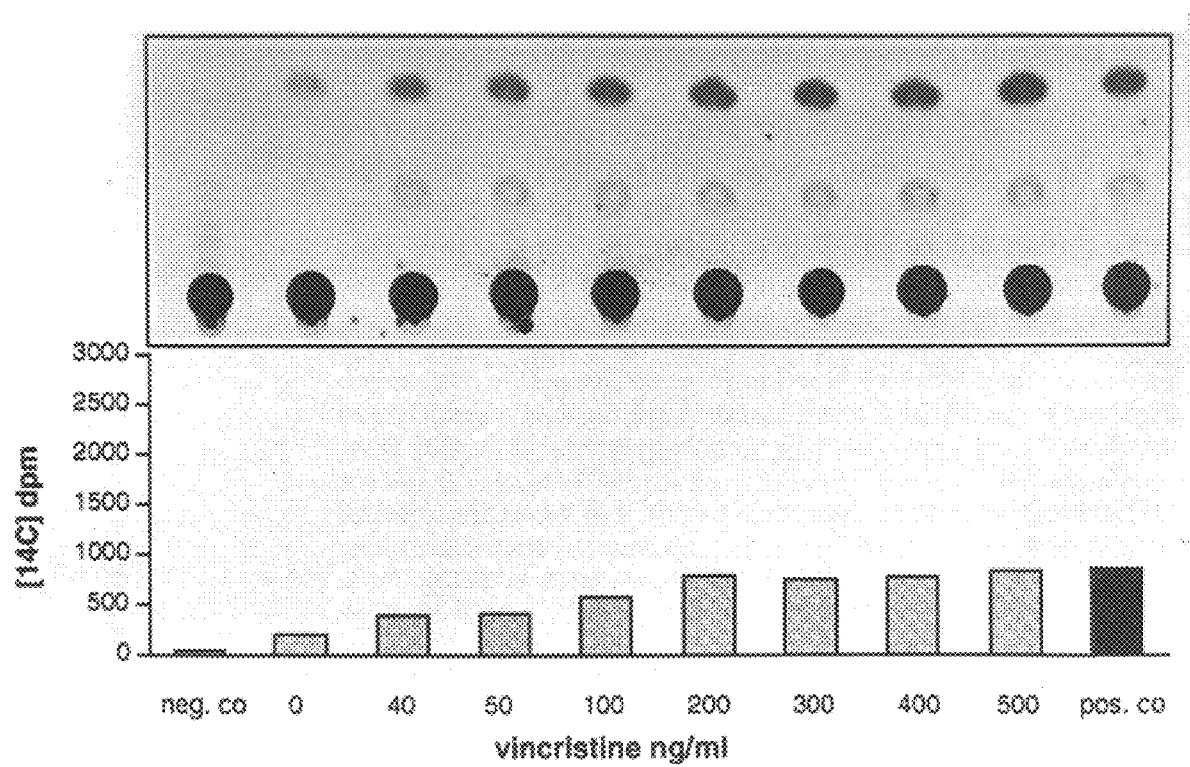

It has previously shown that the mdr1 promoter is drug-inducible to a certain extent (Kohno et al, 1989). We performed drug-induction studies using the MDR associated drug vincristine in a wide concentration range (40–500 ng/ml). Forty-eight h after transfection with pCAT-mdrwt cells both lines were treated with vincristine for 24 h. Reporter gene expression was measured in HCT15 and in KM12 cells using TLC (quantitation with the Phospho Imager) as well as LSC. Drug-induced CAT expression was dose-dependent in both transfected cell lines, spanning vincristine concentrations of 40, 50, 100, 200 ng/ml, and reaching a plateau at 200 mg/ml in KM12 and at 300 ng/ml in HCT15 cells (FIG. 4A and 5A).

For a detailed analysis of vincristine-induction in the two cell lines, CAT expression levels were compared with the basal CAT expression in transfected, but non-induced cells (expressed by IF), as summarized in FIG. 6. In HCT15 cells expressing high intrinsic MDR, the drug-induction was significantly enhanced in comparison to the sensitive KM12 cells. Taking the dpm-values (FIG. 6) of LSC measurements for the 40 ng/ml vincristine treatment, the induced CAT expression in HCT15 was almost 3 fold increased compared to KM12 ($P<0.0003$); for the 400 ng/ml vincristine treatment, a 2.5 fold higher induction in HCT15 compared to KM12 ($P<0.0025$).

These results demonstrate a much wider range of a dose-dependent drug-induced mdr1 promoter driven CAT gene expression, than previously described (Kohno et al, 1989; Asakuno et al, 1994). The inducibility of the mdr1 promoter region at drug concentrations in the range of therapeutic relevance point to a possible molecular mechanism of mdr1 gene activation and development of MDR phenotype during chemotherapy which supplements knowledge of gene amplification.

In summary, the induction level of the transfected CAT reporter gene by the MDR relevant drug vincristine is not only drug concentration dependent, but also cell type specific with respect to the MDR characteristics of the cell lines. As described by Frommel et al. 1993, variable mdr1 gene induction by the differentiating agent sodium butyrate was found in colon carcinoma cell lines, naturally different concerning their MDR characteristics. This, and data from Kohno et al. 1989, describing variations in mdr1 promoter activities in drug-sensitive KB and resistant VJ-300 cells further supports the cell type specific inducibility of the mdr1 promoter.

Enhancement of Basal and Drug-induced CAT Expression, Driven by Point Mutated mdr1 Promoters.

To analyze the influence of point mutations within this mdr1 promoter region on the basal and drug-induced CAT gene expression in HCT15 and KM12, both cell lines were transfected with CAT constructs, containing point mutated mdr1 promoter sequences: pCAT-mdr103, harboring the T→C-mutation at position +103, and pCAT-mdr137, harboring the G→T-mutation at position +137 (11). T→C (+103) mutated mdr1 promoter. Comparison of the basal pCATmdr103-versus pCATmdrwt-driven CAT expression demonstrates in HCT15 an 1.3 times higher expression level than those driven by the wildtype mdr1 promoter sequence ($P<0.03$), shown in FIG. 4B. Investigating the basal CAT expression in KM12 cells a 2 times higher level was observed in the pCATmdr103-versus the pCATmdrwt-transfected cells ($P<0.002$), depicted in FIG. 5B. After vincristine treatment of pCATmdr103-HCT15 cells, 1.5 times (40 ng/ml; $P<0.0085$) and 1.43 times (400 ng/ml; $P<0.015$) higher CAT expression levels were measured in comparison to the wildtype promoter driven reporter gene expression. In KM12 cells, the drug-induced CAT expression was 2.2 (40 ng/ml; $P<0.001$) and 2.1 (400 ng/ml; $P<0.0015$) higher than those in the pCATmdrwt-transfected cells (FIG. 6).

These results indicate, that i) the cell type specificity (HCT15 versus KM12) for the basal as well as for the drug-induced CAT induction was retained with the mutant promoter; ii) the induction of the CAT expression was significantly higher in cells driven by the T→C (+103) mutated promoter than by the wildtype promoter in HCT15 ($P<0.0003$), as well as KM12 ($P<0.0002$), and iii) the dose-dependent induction of mutated promoter driven CAT expression was again observed in both cell lines regardless of their MDR characteristics.

Figure 5B:
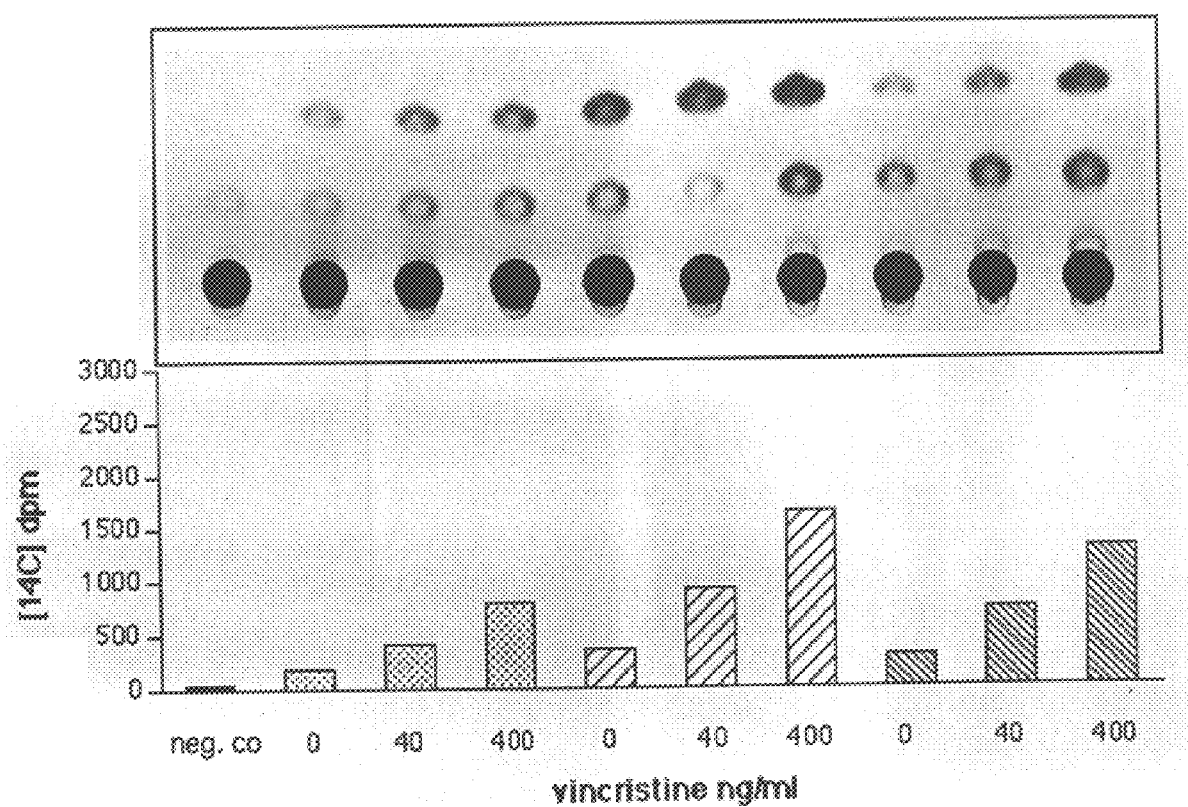

G→T (+137) mutated mdr1 promoter. Analysis of both basal and drug-induced CAT expression in HCT15 cells revealed a higher, but not significantly elevated expression level (FIG. 4B), if compared to pCATmdrwt-transfected cells. By contrast, basal CAT expression level ($P<0.01$) as well as induced CAT expression after vincristine treatment with 40 ng/ml and 400 ng/ml were significantly higher ($P<0.005$) in KM12 cells in relation to the wildtype promoter driven expression (FIG. 5B).

In summary, i: the cell type specificity (HCT15 versus KM12) for basal and induced CAT expression was again demonstrated; ii: the induction of the CAT expression in the pCAT-mdr137- vs. pCAT-mdrwt-transfected cells was not significantly increased in HCT15 cells, but was significantly higher in KM12 cells; and iii: the CAT induction was again dose-dependent in both cell lines (FIG. 6). Several transcriptional activators as well as "stress" response elements for the mdr1 promoter are known. In addition to other elements (e.g. −136 to −76), a drug response element spanning +1 to +121 of the sequence downstream the initiation site has been described as necessary for stress induction of mdr1 promoter activity (Uchiumi et al, 1993). The CAT-constructs used in this study contain mdr1 promoter sequences, originally isolated by PCR from human osteosarcomas (Stein et al, 1993) and include this specific response element (+1 to +121). Both, the wildtype pCAT-mdrwt and pCAT-mdr137 construct carry this sequence in the non-mutated form, whereas pCAT-mdr103 possesses a point mutation in exactly this region causing a dramatic increase in basal CAT expression and in drug inducibility in the two tumor cell lines. These effects, mediated by a point mutation which was found in human tumors may provide a further explanation for the activation of mdr1 gene expression in tumors, since it has been reported that mdr1 overexpression is not frequently associated with gene amplification (Kohno et al, 1994). These results are in agreement with our earlier investigations in COS cells using vincristine and adriamycin for the induction of CAT expression (Stein et al, 1994). The present data will support the suggestion that alterations in gene regulation of mdr1, such as changes in promoter activities or variations in cell specific transcription factor levels may represent important mechanisms in the upregulation of mdr1 expression. Furthermore, the demonstrated drug inducibility and activity in tumor cells with varying intrinsic MDR phenotype suggests that the mdr1 promoter may be an attractive candidate for inclusion in expression vectors aimed at gene therapy of multidrug resistant tumor cells.

EXAMPLE 5

Increased mdr1 gene expression has been detected in a variety of human cancers (Nooter et al, 1991). The mechanism responsible for this overexpression is not yet understood. Several lines of evidence suggest regulation at the transcriptional level (Goldstein et al, 1989). Two transcriptional start sites of the mdr1 gene have been identified (Ueda et al, 1987): a downstream promoter from which the majority of transcripts are derived, and an upstream promoter region, which is until now poorly characterized. In a collection of human bone and soft tissue sarcomas, we have discovered high intrinsic mdr1 expression in all osteosarcomas analysed, but low intrinsic expression in MFHs irrespective of bone or soft tissue origin (Stein, et al, 1993). Thus, sequencing and transient expression analysis of mdr1 promoter regions in osteosarcomas versus MFHs should be helpful to understand the mechanism of overexpression in more detail. While no sequence alterations were found in MFHs, point mutations were detected in the mdr1 promoter region of osteosarcomas. These mutations may be critical for mdr1 overexpression, as suggested by the inducibility of the reporter gene CAT.

Tumors

Tumor samples were obtained from Drs. P. Schmidt-Peter and W. Haensch as described (Stein et al, 1993). Sarcomas with distinctly different intrinsic mdr1 expression levels were chosen for this study: 9 osteosarcomas with high mdr1 expression and 8 bone or soft tissue derived MFHs with low mdr1 expression (Stein et al, 1993). High molecular weight DNA was isolated from frozen tumors (−70° C.) according to standard protocols.

Northern Analysis

Isolation of total cellular RNA from frozen tumors and hybridization conditions were as previously described (Stein et al, 1993). 10 mg of each tumor RNA were subjected to Northern analysis. Nylon membranes were hybridized to a $^{32}$P-labelled mdr1-specific RNA probe pHDR 5.A (Chen et al, 1986; ATCC-No. 61360). Hybridizations with a GAPDH (glyceraldehyde-phosphate dehydrogenase) DNA probe were done to evaluate uniform RNA loading.

Recombinant Plasmids

A region of the human mdr1 downstream promoter sequence (−207 to +158; nomenclature according to Kohno et al, 1990) was generated by PCR under the following conditions: 94° C. 1 min; 45° C. 1 min; 72° C. 2 min; 30 cycles. The "Gene Amp PCR Reagent Kit with Ampli Taq DNA Polymerase" (Perkin-Elmer GmbH, Überlingen) and two human mdr1 specific oligonucleotides were used: 5'-GAATTC-CTTGCCCTTTCTAG-3' (−207 to −194) including the Eco RI restriction site as the 5'-primer and 5'-GGATCC-AGTAGCTCCCAGCTT-3' (+144 to +158) including the Bam HI restriction site as the 3'-primer (Kohno et al, 1990). 100 ng of each high molecular weight DNA from human sarcomas served as template for at least two independent PCR experiments. PCR fragments and the plasmid pBluescript M13 (Stratagene, San Diego, Calif.) were digested with Eco RI and Bam HI and ligated to generate clones pM13mdr1 to pM13mdr9 (for osteosarcomas) and pM13mdr10 to pM13mdr17 (for MFHs). To analyze anticancer drug inducibility by CAT-ELISA, PCR-fragments of each two plasmids containing mdr1 promoters with the T→C-mutation at +103 (pM13mdr3 and pM13mdr5), or with the G→T-mutation at +137 (e.g. pM13mdr7 and pM13mdr8), or with the wild-type promoter (e.g. pM13mdr10 and pM13mdr11), were digested with XbaI. To generate CAT constructs containing the digested mdr1 fragments, the pUCAT vector was created by insertion of a 1.36 kb-HindIII/Bam HI-fragment of pSV2CAT, with a HindIII site converted to a XbaI site, into the XbaI/Bam HI-digested pUC18. The XbaI-digested PCR-fragments were cloned into the XbaI-digested pUCAT, resulting in clones pCATmdr3 and pCATmdr5 (T→C), pCATmdr7 and pCATmdr8 (G→T), and pCATmdr10 and pCATmdr11 (wild-type).

Sequencing

All pM13mdr clones were sequenced according to the "Sequenase Version 2.0" protocol (United States Biochemicals, Cleveland, Ohio), by using the universal primer 5'-GTTTTCCCAGTCACGAC-3' supplied with the kit and [$^{35}$S]dATP (Amersham Buchler GmbH & Co KG, Braunschweig). Transient transfection and treatment with MDR relevant drugs The African green monkey kidney cell line COS was maintained in DMEM (Gibco BRL, Eggenstein) supplemented with 10% fetal calf serum at 37° C. and 5% $CO_2$. COS cells ($5 \times 10^5$ per 60 mm dish) were grown and transfected with 10 mg of each linearised pCAT-mdr construct (pCATmdr3 and pCATmdr5; pCATmdr7 and pCATmdr8; pCATmdr10 and pCATmdr11) by electroporation (100 V; 250 mF)(Chu et al., 1987). pSV2CAT and pUCAT, respectively, served as positive and negative controls. 48 h after transfection, 20 ng/ml or 50 ng/ml of each anticancer drug (vincristine from Eli Lilly, Indianapolis, Ind.; doxorubicin as adriablastine from Farmitalia, Freiburg), dissolved in 0.15 M NaCl, were added for 24 h at 37° C. before the CAT-assay was performed. Untreated controls were harvested at the same times as treated cells.

CAT-ELISA

The assay was carried out with the kit from Boehringer, Mannheim. Promoter activity was determined as CAT expression using a non-radioactive digoxigenin labelled anti-CAT antibody, following the conditions recommended by the manufacturer. Cell extracts were prepared by using the supplied lysis buffer. The protein concentration was 150 µg/well of a 96 well microtiter plate. An increase in sensitivity was obtained by using the substrate enhancer, supplied by the manufacturer. The blank value was subtracted automatically in the microplate reader.

Statistical Analysis

To evaluate the statistical significance of the drug-induced CAT-activity, the control group driven by the wild-type mdr1 promoter sequence was compared to the groups driven by the mutant promoter sequences in each CAT-assay using Student's t-test.

Northern Analysis

Tumor samples were selected from a panel of 61 sarcomas of adult patients investigated for frequency and extent of mdr1 expression in our previous study (Stein et al, 1993). None of the patients had received chemotherapy. The availability of related tumor types with high versus low mdr1 expression levels was a prerequisite for the experiments reported here. Investigations described concern those types of tumors that had shown high mdr1 expression levels at a high frequency, i. e., the 9 osteosarcomas shown in FIG. 7A, and tumors for which only low or intermediate mdr1 expression levels at a low frequency had been observed, i. e., the 8 MFHs shown in FIG. 7B.

mdr1 Promoter Analysis in Human Sarcomas

After isolation of DNA from the osteosarcomas and MFHs, the mdr1 promoter region (−207 to +158) was amplified by PCR and sequenced. The reason for analyzing this particular region was the presence of a drug responsive element within this sequence (Kohno et al, 1989; Uchiumi et al, 1993; Ferrandis et al, 1993). To ensure the validity of the results, all experiments (PCR amplification, cloning and sequencing) were done at least two times per tumor.

In a series of clones containing the amplified PCR products from 9 osteosarcomas, 2 distinct point mutations were detected (data not shown): The first was a T→C-transition at position +103 present in 2 out of 9 osteosarcoma-derived clones (pM13mdr3 and 5). A second type of mutation, a G→T transversion at position +137, was detected in 5 out of 9 osteosarcoma-derived clones (pM13mdr2, 4, 7, 8, 9). No other deviations from the wild-type sequence (normal human placenta; Kohno et al, 1990) were observed within the region analysed. The remaining 2 osteosarcomas showed no changes in the mdr1 promoter region.

A different picture emerged from the analysis of MFHs, a prototype of human sarcomas with low mdr1 expression. In 8 cases (4 each of either bone or soft tissue origin) the sequence was unchanged throughout the entire mdr1 promoter region.

From these results it was tentatively concluded that a correlation may exist between mdr1 expression level and the occurrence of certain point mutations in the mdr1 promoter. In order to further substantiate this notion we performed CAT analyses with mutant and wild-type mdr1 promoter sequences in the presence or absence of drugs that belong to the MDR family.

Effect of Anticancer Drugs on Mutant mdr1 Promoter Sequences

A set of CAT constructs containing the mutant (T→C or G→T) or wild-type mdr1 promoter sequences was generated in order to analyze the influence of these point mutations on promoter activity and responsiveness to anticancer drugs.

COS cells were transfected with each of these CAT containing plasmids. Treatments with vincristine and doxorubicin at concentrations of 20 ng/ml or 50 ng/ml, respectively, were started 48 h after transfection.

As far as CAT expression driven by the wild-type or mutant mdr1 promoter region is concerned, no differential effects on basal promoter activity were observed (FIG. 8). This level of activity was, therefore, taken as 100% to evaluate the potential influence of a treatment with MDR relevant drugs.

CAT expression in pSV2CAT transfected COS cells (positive control) was more than 4–5 times higher than in COS cells transfected with the different mdr1 promoter sequences. In pUCAT transfected cells (negative control) CAT expression was below the level of detection (not shown).

Treatment with drugs of the MDR family led to a remarkable induction of CAT expression in all cell clones irrespective of the mdr1 promoter sequence (FIG. 8). Both anticancer drugs caused a comparable degree of induction in a given experiment.

In COS cells transfected with CAT constructs containing the wild-type or the G→T-mutant promoters, reporter gene expression was about 146% and 143% after exposure to vincristine or doxorubicin, respectively, relative to untreated controls (100%). However, in cells transfected with CAT constructs driven by the T→C-mutant mdr1 promoter sequence, a significantly higher induction ($p<0.05$) was found: in the case of vincristine CAT expression reached a level of 191%, in the case of doxorubicin a level of 184% (FIG. 3). All results were averaged from 5 independent experiments. Standard deviations from the means were $\leq 15\%$.

These results point to a direct link between the T→C-mutation at position +103 within the mdr1 promoter and increased inducibility by MDR relevant drugs resulting in enhanced expression of the reporter gene, and possibly of the mdr1 gene in cancer cells.

There is now general agreement that structural alterations in a number of genes (proto-oncogenes, tumor suppressor genes, etc.) may account for the onset and development of human cancer. Increased mdr1 gene expression is thought to be associated with the progression of many cancers. Whereas amplification of the mdr1 gene is a common event that accompanies increased expression in cell lines but not in clinical tumors (Goldstein et al, 1989), the occurrence of point mutations has so far appeared to be rather an exception, resulting from mutations in the mdr1 gene coding region in association with drug selection (Choi et al, 1988). To our knowledge, point mutations in the non-coding region of the mdr1 gene have as yet not been reported, neither in osteosarcomas nor in any other human tumors. Both types of point mutations in the promoter region observed in the present study were repeatedly found in untreated tumors. With respect to these particular mdr1 promoter mutations it would be interesting to learn, first, whether they occur in both mdr1 alleles, second, whether they occur in other types of tumors and in which frequency; third, whether they are detectable not only in adult (this study) but also in pediatric osteosarcomas, which could lead to the question of somatic versus germ-line origin; and finally, whether these promoter mutations represent hotspots possibly located at potential binding sites for factors involved in transcriptional regulation.

According to our present knowledge, the expression of mdr1 genes is regulated in a cell type-specific manner (Chin et al, 1993; Ferandis et al, 1993). Differentiation-inducing agents (e.g., retinoic acid) are able to induce mdr1 gene expression (Bates et al, 1989). We speculate that the acquisition of +103 or +137 mutations in the mdr1 promoter and the concomitant increase of mdr1 expression may in some way subvert specific differentiation steps in immature precursor cells, subsequently giving rise to osteosarcomas. It remains to be investigated at which developmental stage, if any, such mutations may occur, by which mechanisms they may be induced, and whether they do indeed predispose to osteosarcomas.

In addition to its role in drug resistance, P-glycoprotein may serve further functions in normal tissues and malignant tumors (Ronison et al, 1991). For example, in human colon and breast carcinomas, a correlation between mdr1 expression and tumor malignancy has been recently described (Weinstein et al, 1991; Hennequin et al, 1993). This may indicate that cells expressing the mdr1 gene at a high level might possess a selective growth advantage. In the absence of drug exposure cells may acquire the same property by mutations of the type described above thus explaining the observed high prevalence of such particular mutations.

In view of the occurrence of p53 mutations in human osteosarcomas (Diller et al, 1990), attention should also be paid to possible specific interactions of mutant p53 with mdr1 promoter sequences (Chin et al, 1992) leading to transcriptional regulation (Zastawny et al, 1993) or to gain-of-function activities (Dittmer et al, 1993). It is conceivable that point mutations beyond the core sequences (Zastawny et al, 1993) in the mdr1 promoter could affect this type of interaction.

An interesting result emerged from the functional analysis of the different mdr1 promoter sequences in the CAT assay. Although these constructs could not be distinguished in their effects on basal CAT expression, they responded differentially to anticancer drugs. Previous studies have identified responsive elements within mdr1 promoters mediating transcriptional activation by various forms of environmental stress (Uchiumi et al, 1993; Chin et al, 1990). A specific drug responsive element, inducible by treatments with anticancer drugs such as vincristine and doxorubicin, has been located at position −136 to −76 (12). Our finding, that in the presence of a point mutation at position +103, mdr1 promoter activity is further stimulated following treatment with the same drugs, suggests a role of additional sequences distant from the known drug responsive elements. In summary, our results indicate a correlation between a specific point mutation in the mdr1 promoter sequence and responsiveness to drugs of the MDR family.

EXAMPLE 6

Gene Transfer of Human TNF-α into Glioblastoma Cells Permits Modulation of mdr1 Expression and Potentiation of Chemosensitivity Construction of Retroviral Vector The Murine Leukemia Virus-derived retroviral vector N2A (Hantzopoulos et al., 1989) was used for the insertion of the human TNFα cDNA. The plasmid pN2tk-hTNF was constructed by insertion of the 1.05 kilobase (kb) SacII/KpnI-fragment from pM13-hTNF (in which the KpnI site was converted to blunt end) into the SacII/Mlu I (the Mlu I site was also converted to blunt end) site within the 3'-long terminal repeat of the vector. The expression of the hTNF gene is driven by the herpes-simplex-thymidine kinase (tk) promoter (kindly provided by M. Strauss, Berlin), which was fused to the cytokine gene (FIG. 9).

Cell Culture

The U373MG human glioblastoma cell line was obtained from the Tumorbank, DKFZ, Heidelberg. The cells were maintained in Dulbecco's modified Eagle's Medium (GIBCO, Paisley, UK) supplemented with 10% fetal calf serum (Biochrom, Berlin, Germany) and 2 mM L-glutamine. The mouse fibrosarcoma L929 cell line (Flick and Gifford, 1984) was grown in RPMI 1640 medium (GIBCO) containing 10% fetal calf serum (Biochrom).

Electroporation

The pN2tk-hTNF retroviral vector was introduced into U373MG glioblastoma cells by using the electroporation method. For the procedure, cells were trypsinized, centrifuged and the cell pellet was resuspended in ice cold phosphate-buffered saline (PBS). The cell concentration was adjusted to $1\times10^6$ cells/ml. 10 mg linearized vector DNA were added and cells were kept on ice for 10 minutes, electroporated at 960 mF, 250 V in an Gene Pulser apparatus (BIORAD, Hercules, Calif.) and kept on ice for another 10 minutes. The neomycin resistant cell clones were selected in 0.5 mg/ml Geniticin (GIBCO) and expanded for further investigations.

RNA Analysis

Total cellular RNA was isolated from $5\times10^5$ cells using the LiCl/urea procedure (Auffrey and Rougeon, 1980). For Northern blot analysis 10 mg total cellular RNA were separated on 1.2% agarose gels containing 5% formaldehyde and blotted to Hybond-N$^+$ membranes (Amersham/Buchler, UK). The membranes were hybridized to TNFα-specific $^{32}$P-radiolabelled RNA probes using the pM13-hTNF plasmid as template for T7 RNA Polymerase (Stratagene, La Jolla, Calif.).

TNFα Cytotoxicity Assay

The biological activity of hTNF in the supernatants of transduced cells was determined by a bioassay as previously described (Flick and Gifford, 1984). Prior to the assay fresh medium was added to the glioblastoma cells and after 24 hours supernatants were harvested.

L929 TNFα-sensitive cells were seeded into 96-well microtiter plates (Costar, Cambridge, Mass.) at a concentration of $1\times10^4$ cells per well in phenol red-free RPMI medium containing 1 mg/ml actinomycin D (Sigma, St. Louis, Mo.). The serially diluted standard of recombinant human TNFα (SERVA, Heidelberg, Germany) and the test samples were added and the cells were incubated for 18 hours. Cytotoxicity of TNFα to L929 cells was assessed in the 3-(4,5-dimethyl-2-thiazolyl)-2,5-diphenyl-[2H]-tetrazolium bromide (MTT; Sigma, Germany) conversion assay by incubation of cells with 0.5 mg/ml MTT for 4 hours at 37° C. Thereafter, the formazan product was solubilized with 10% SDS, pH 4.5. Absorbance at 560 nm was determined using a microplate reader.

Cell Proliferation Assay

For cell proliferation assay of parental and hTNF-secreting U373MG glioblastoma cells, $1\times10^5$ cells were plated into each well of 6 well plates (Costar) and incubated at 37° C. for at least 5 days. Cell numbers were determined each day using a cell counter (Coulter Counter Model ZM).

Immunohistochemistry

To determine P-glycoprotein expression in hTNF-secreting U373MG glioblastoma cell clones, $5\times10^3$ cells per well were seeded in an eight-chamber slide (Nunc Inc., Roskilde, Denmark) 48 hours prior to detection. The medium was removed and cells were washed three times with PBS followed by fixation with 3.7% formaldehyde for 30 seconds. Cells were washed three times with PBS and incubated with ice cold methanol/acetone (1:1) for 30 minutes at −20° C. The endogenous peroxidase activity was inhibited by incubation with 0.5% $H_2O_2$ in methanol for 10 minutes at room temperature. After washing three times with PBS cells were incubated at room temperature with the monoclonal anti-P-glycoprotein antibody (3 mg/ml) (Clone JSB-1; Boehringer Mannheim, Germany) as primary antibody, which is directed against a conserved internal epitope of P-glycoprotein. Cells were washed three times with PBS and incubated at room temperature for 1 hour with the secondary anti-mouse-Ig-peroxidase antibody (diluted 1:100) (Boehringer Mannheim). The chromogenic development for P-glycoprotein detection was obtained using 3,3'diaminobenzidine (Aldrich, Milwaukee, Wis.) (2.5 mg diaminobenzidine dissolved in 5 ml 0.05 M Tris-HCl, mixed with freshly added 5 ml 30% $H_2O_2$) and the slides were examined under a light microscope.

Rhodamine Assay

To determine the activity of the P-glycoprotein the fluorescent dye rhodamine-123 was used (Sigma, Deisenhofen, Germany) in this functional assay. $5\times10^6$ cells were incubated in phenol red-free RPMI medium supplemented with 5% FCS and 5 mg/ml rhodamine-123 for 15 minutes at 37° C. as described (Pfeil et al., 1994). After the incubation, cells were washed with PBS and split for the following two different incubation conditions: one half of the cells was suspended in PBS plus 250 mM glucose and 0.2% sodium azide and stored at 4° C. At this temperature rhodamine remains within the cells, so that these fluorescent measurements were taken as influx values. The other half was suspended in phenol red-free RPMI with 5% FCS and incubated for 1 hour at 37° C. These conditions are sufficient for P-glycoprotein to exert its function. After washing with PBS plus 250 mM glucose, these cells served as indicators for dye efflux (efflux value). The fluorescence was recorded on a Shimadzu RF 5001 PC spectrofluorometer with excitation at 534 nm and emission at 504 nm, expressed as fluorescence intensity. The relative fluorescence is expressed as percent of the control value obtained by incubation at 4° C., based on the same number of cells ($1\times10^6$ cells).

Cytotoxicity Assay

For the cytotoxicity assay $5\times10^4$ cells were poured into 96-well microtiter plates (Costar) and after 24 hours the cytostatics vincristine (Eli Lilly, Indianapolis, Ind.) or doxorubicin (Farmitalia, Freiburg, Germany) were added with a final concentrations of 10 ng/ml, 50 ng/ml, 300 ng/ml, 500 ng/ml 800 ng/ml and 1000 ng/ml, respectively. Cells were incubated for 3 days at 37° C., then washed with PBS. 100 ml 0.5 mg/ml MTT (Sigma) was added to each well and left to react for 3 hours at 37° C. as described (Carmichael et al., 1987; Walther and Stein, 1994). The formazan dye was solubilized with 150 ml 10% SDS, pH 4.5 and the absorbance was measured at 540 nm in a microplate reader. Absorbance of untreated controls was taken as 100% survival and the percentage inhibition was calculated as follows:

$$\text{inhibition \%} = \frac{100 \times (T - B)}{(U - B)}$$

(T, treated: absorbance determined when tumor cells are exposed to drugs; U, untreated: absorbance of untreated cells; B, blank: absorbance when neither the drug nor MTT was added.

Statistical Analysis

To estimate statistical significance of hTNF-mediated enhancement of chemosensitivity, untransfected control groups were compared to transfected hTNF-secreting groups by using Student's t-test.

Transfer of the pN2tk-hTNF Retroviral Vector and Establishment of TNFα-secreting Glioblastoma Cell Clones To evaluate the effects of transduced hTNF on P-glycoprotein function, stably transfected U373MG glioblastoma cell clones were established by G418 selection.

After 14 days of selection cell clones were isolated and expanded in RPMI medium containing 0.5 mg/ml G418. RNA was isolated and supernatants were harvested to determine hTNF expression and secretion in transfected cell clones. As shown on the Northern blot (FIG. 10) all three clones selected for the study express hTNF-specific transcripts of 1.8 kb (FIG. 10, lanes 3–5) at high levels. The TNF transcripts, driven by the internal tk-promoter are accompanied by transcripts of larger sizes (>5 kb), representing transcripts driven by the viral LTR. However, the parental cells and the clone transfected with the empty vector showed no TNF-specific signal. The high expression of hTNF on RNA level corresponded well to the cytokine level released into the medium. FIG. 11 depicts the amounts of secreted hTNF measured in the supernatants of U373MG cell clones using the TNF-sensitive cell line L929 in a cytotoxicity assay. This assay allows not only to estimate the level of secreted hTNF but also to verify its biological activity. Neither the parental U373MG glioblastoma cells, nor the clone transfected with the pN2A vector produced detectable amounts of the cytokine, whereas the pN2tk-hTNF carrying clones secreted significant amounts of biologically active hTNF within 24 hours. The expression and production of the cytokine was detectable in Northern-blot analysis and in L929 cytotoxicity assay over a period of 3 months.

Growth Characteristics of TNFα Secreting Glioblastoma Cells

Figure 12:
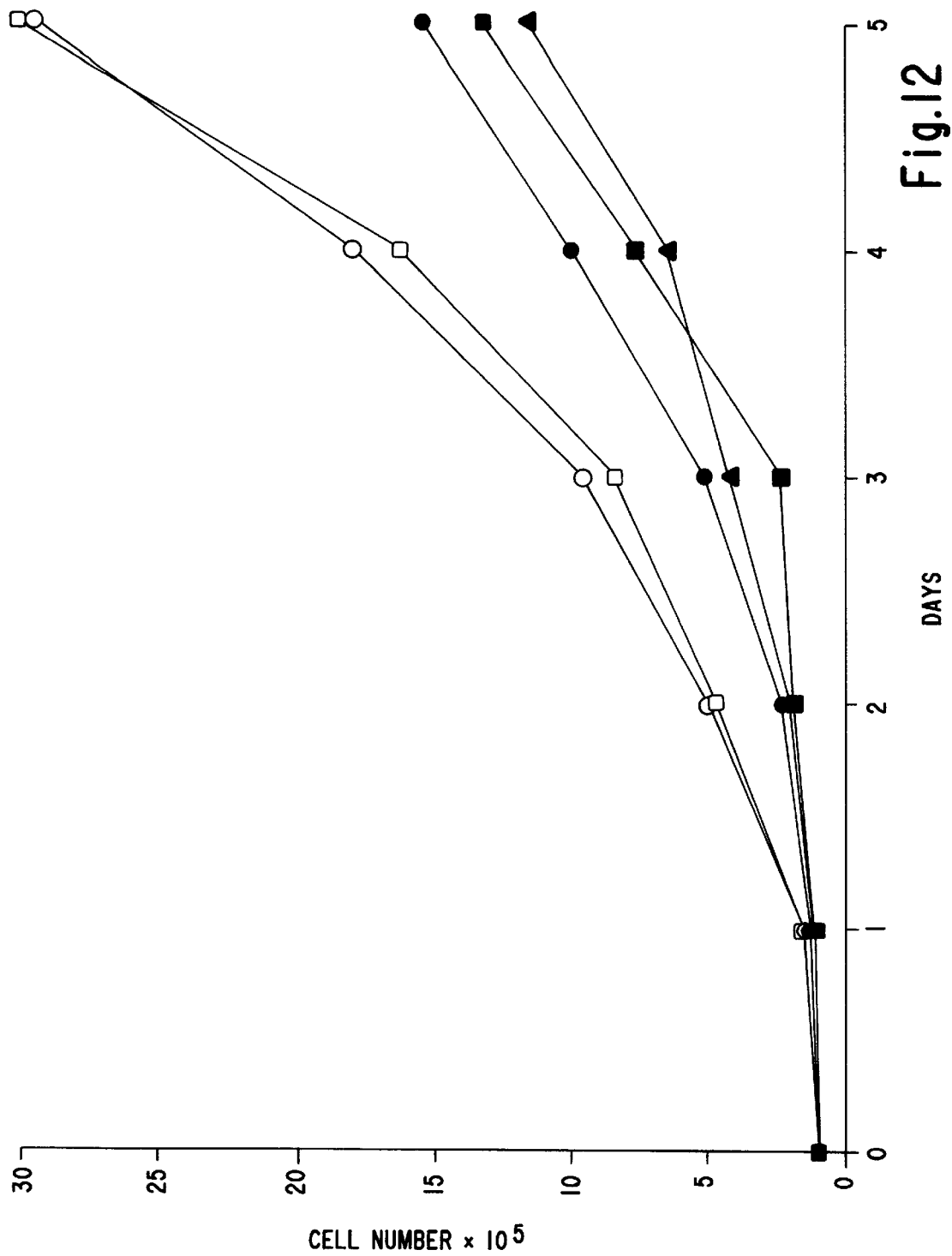

Before analyzing the effects of transduced hTNF on the function of P-glycoprotein, the influence of the secreted cytokine on the growth behavior was determined. Control cells and the transfected clones were grown for five days starting with $1 \times 10^5$ cells. The cell number was counted in triplicates each day using Coulter Counter. FIG. 12 demonstrates that the growth rates of transfected cell clones are influenced by the secreted hTNF: slight differences were observable after the second and third day of cultivation, however at the fourth and fifth day all cytokine secreting clones showed a significantly reduced cell proliferation (up to 50% reduction in cell growth) compared to the nontransfected parental glioblastoma cells and the empty vector carrying tumor cells. This finding would suggest that the constitutively expressed and secreted hTNF levels are cytostatic to these tumor cells, supporting our earlier observations in other cell lines (Walther et al., 1993; Sparmann et al., 1994).

P-glycoprotein Expression in Transfected TNFα-secreting Glioblastoma Cells.

The expression of P-glycoprotein was assessed in the stably pN2tk-hTNF transfected U373MG glioblastoma cell clones and was compared to the appropriate control cells. Parental tumor cells as well as tumor cells carrying the empty vector construct stained similarly well with the JSB-1 anti P-glycoprotein antibody, indicating no difference in their high intrinsic P-glycoprotein expression (data not shown). However, in all five hTNF-gene transduced cell clones, a dramatic reduction in P-glycoprotein expression has been observed, reflected by the less intense staining of these cells with the antibody. This reduction in P-glycoprotein expression shows variations in dependence of the amount of cytokine released by the different glioblastoma clones: the clone U373 pN2tk-hTNF1 which produced less hTNF than the clones U373 pN2tk-hTNF2 and pN2tk-hTNF3, developed a detectable staining, whereas the other two did not. This indicates that the secretion of hTNF is able to reduce P-glycoprotein expression in tumor cells, which originally possess high expression levels of this protein and that this hTNF-mediated effect seems to be dependent on the amount of the secreted cytokine.

Rhodamine-123 assay in TNFα-secreting Glioblastoma Cells

To investigate whether the hTNF-mediated reduction in P-glycoprotein has an influence on the influx/efflux-ratio of MDR-relevant drugs, the fluorescent dye rhodamine-123 was used for functional analysis in transduced glioblastoma cells. The P-glycoprotein is active in transporting rhodamine-123 so that the intensity of fluorescence in the cells reflects the ability of the cell to extrude the dye via the P-glycoprotein. As shown in Table II, both, the parental tumor cells and the empty vector carrying cells possess a high efflux rate of rhodamine-123 reflected by the dramatic reduction in fluorescence intensity 1 hour after incubation at 37° C. compared to influx fluorescence intensities being measured in those cells fractions, which were kept at 4° C. after 15 minutes of rhodamine-123 uptake (see Materials and Methods). The enhanced P-glycoprotein activity in the control cells is also expressed by their low value of relative fluorescence. In sharp contrast to the control cells, the three transduced glioblastoma clones behave differently: in all three clones an elevated rhodamine uptake could be measured. Furthermore, the efflux of the fluorescent dye was dramatically reduced causing elevated dye accumulation, reflected by the significant higher efflux fluorescence intensities and higher relative fluorescence values in these cells (FIG. 13). Again, this effect seemed to be dependent on the amount of the secreted hTNF, since clone U373 pN2tk-hTNF1 with the relative lower hTNF secretion (FIG. 11) has also higher efflux rates compared to the other two cell clones.

To underline the measurements in the functional rhodamine-123 assay, additionally fluorescence microphotographs were taken from those cell fractions which served as the efflux preparations in the previously described rhodamine assay experiments. The control cells showed no detectable dye fluorescence, whereas the transfected cell clones show bright fluorescence (data not shown). These observations indicate that the secretion of hTNF induces a low efflux in the transfected cells causing a significant rhodamine accumulation within the cells. This effect correlates well with the demonstrated reduction in P-glycoprotein expression.

Influence of TNFα-secretion on cytotoxicity of vincristine and doxorubicin. Both the immunohistochemical analysis and the functional rhodamine-123 assay have shown that the production of transduced hTNF in U373MG glioblastoma cells down-regulates mdr1 expression and modulates its biological function. In result of these effects we assumed that secreted hTNF should therefore influence cytotoxicity of MDR relevant drugs such as vincristine and doxorubicin.

It was tested to what extent transduced hTNF enhances the cytotoxicity of vincristine and doxorubicin compared to the untransfected parental U373MG glioblastoma cells and to the empty vector harboring cells.

In a series of experiments the $IC_{50}$ (inhibition concentration for 50% cytotoxicity) for both drugs was estimated for the control cells and the three transduced clones respectively. For the assessment of hTNF effects at different drug concentrations, a concentration range was chosen for vincristine and doxorubicin, which exerts a maximum cytotoxicity of 20% in the parental U373MG control cells. As shown in FIG. 14, the presence of hTNF dramatically enhances the cytotoxicity of vincristine in the transduced cells. The same effect is shown in FIG. 15 for doxorubicin, although it does not reach the inhibition level of vincristine. Thus, it can be concluded that secretion of the transduced hTNF in glioblastoma cells and addition of MDR relevant drugs increases synergistically the antitumor effect of these substances. To support this conclusion, FIG. 16 shows the $IC_{50}$ for vincristine and doxorubicin in both, nonproducing and cytokine releasing cells. These data give further evidence that the cytokine acts synergistically with both drugs. This is also reflected by the high dose modifying factor values of 17 to 36 fold increase in cytotoxicity. Thus, transduction and secretion of hTNF not only influences the P-glycoprotein expression, but has also a dramatic impact on the cytotoxicity of MDR-relevant drugs. This in fact might point to the possibility of a more efficient combination of cytokine gene transfer and chemotherapy in the treatment of certain human tumors such as malignancies of the brain.

The development of MDR in many tumors of different origin creates the major obstacle in chemotherapeutic treatment of malignancies. To overcome this phenomenon various approaches have been made. Substances that interfere with the P-glycoprotein activity, such as calcium channel blockers, nontoxic lipophilic drugs or calmodulin inhibitors were used (Hofsli and Nissen-Meyer, 1990; for review see: Kellen, 1993). However, the use of P-glycoprotein antagonists is not without controversy. Therefore the development of alternative strategies to overcome MDR in tumors is focused on the modulation of P-glycoprotein expression in resistant tumors. It is well known that brain tumors including gliomas have poor prognosis which is in a high percentage based on their resistance to chemotherapy. This in fact stimulated many investigators to study the effects of immunotherapies with TNFα, interferon, IL-2 or lymphokine activated killer cells as well as polychemotherapy in combination with biological response modifiers (Del Maestro et al., 1992; for review see: Jaeckle, 1994). Among these approaches the combined therapy with human TNFα and anticancer drugs, which are often MDR relevant drugs, has shown that this cytokine has the potential to enhance the cytotoxicity of these substances in various tumor models including glioblastomas (Regenass et al., 1987; Valenti et al., 1993). However, many studies with TNFα demonstrated that this cytokine, although a powerful anticancer agent, exerts severe toxic side effects if administered systemically to cancer patients in clinical trials (Schiller et al., 1991; Yoshida et al., 1992). Therefore the gene transfer of the human TNFα gene directly into the tumor cells is an attractive alternative to circumvent these disadvantages. Furthermore, the release of the cytokine into the tumor environment could exert more efficient antitumor activity associated with stimulation of immune response or might lead to alterations in the malignant cells sensitizing to other treatments such as chemotherapy.

We have investigated the in vitro-effects of human TNFα which has been secreted by transduced U373MG human glioblastoma cells. Consistent with earlier studies (Walther et al., 1993; Sparmann et al., 1994), the hTNF-expressing glioblastoma clones showed a reduced cell proliferation supporting the assumption that transduction of secretory hTNF has a significant cytostatic effect on tumor cells. Beside this fact, it was of greater interest to investigate whether transduced hTNF is able to alter the expression and function of the P-glycoprotein, which was found to be highly expressed in brain tumors causing resistance to several chemotherapeutic drugs (Matsumoto et al., 1991). It has been demonstrated in different investigations that externally added cytokines are able to modulate the expression of P-glycoprotein in myeloma cells and colon carcinoma cell lines (Evans and Baker, 1992; Walther and Stein, 1994). The genetically engineered hTNF-secreting U373MG glioblastoma cells also possess altered P-glycoprotein expression as shown in this report on protein level by immunohistochemistry. Compared to their untransfected parental tumor cells the P-glycoprotein level was significantly reduced in hTNF-secreting glioblastoma cells. This reduction in P-glycoprotein expression also led to functional alterations in these cells, changing their behavior in drug uptake and efflux. As demonstrated in experiments with the fluorescent dye rhodamine-123, hTNF production did not only enhance the dye uptake in these cells but more importantly caused a significant drop in rhodamine efflux reflected by the 3 to 5.6 fold enhanced relative fluorescence in these cells (FIG. 13). Fluorescence microphotographs gave further evidence for the dye accumulation in the transduced tumor cells. The hTNF-mediated effects on P-glycoprotein expression and function should have an impact on the cytotoxicity of MDR relevant drugs as well. As shown in previous studies with human colon carcinoma cell lines, the external long term application of hTNF for up to 48 hours enhanced the antitumor activity of MDR relevant drugs in association with modulation in mdr1 expression (Walther and Stein, 1994). The cytotoxicity assay provided the evidence whether hTNF-secretion can potentiate the antitumor activities of vincristine and doxorubicin. These experiments (FIGS. 14 and 15) showed the dramatic, synergistic increase in drug cytotoxicity for both agents, which was clearly restricted to the transduced cell clones. The elevation of basal drug cytotoxicities from maximum inhibition levels of 17.5% for vincristine and 10.5% for doxorubicin in the parental tumor cells to a maximum of 96.5% and 70% in the transduced cells, respectively, underlines the significance ($P<0.005$) of the combined effects of hTNF and these drugs based on P-glycoprotein modulation. Interestingly, the hTNF-mediated effects seemed to be dependent on the amount of the secreted cytokine. Both glioblastoma clones producing 7.85 ng/ml hTNF and 8.2 ng hTNF/ml, respectively, showed stronger reduction in P-glycoprotein expression associated with higher drug accumulation rates, and developed higher cytotoxicities ($P<0.05$) than the clone releasing 5.78 ng hTNF/ml. This suggests how important it might be to achieve hTNF levels that are efficient enough to exert optimal MDR overcoming effects in resistant tumor cells. This in fact remains to be investigated by using conditional expression vector systems with e.g. inducible promoter sequences. Studies of Culver and Ram (Ram et al., 1993) for retroviral gene transfer of the thymidine kinase suicide gene in brain tumors underline the attractiveness of glioblastomas as candidates for gene therapy. The transduction and expression of the human TNFα gene in human glioblastoma cells in vitro is an indication that the combination of hTNF gene transfer and chemotherapy can lead to a more efficient treatment of resistant human tumors by overcoming their MDR phenotype.

REFERENCES

A. Dusty Miller. Nature 357: 455–460, 1991;

Asakuno, K., Kohno, K., Uchiumi, T., Kubo, T., Sato, S., Isono, M., and Kuwano, M. Involvement of a DNA binding protein, MDR-NF1/YB-1, in human mdr1 gene expression by actinomycin D. Biochem. Biophys. Res. Comm., 199: 1428–1435, 1994.

Auffrey, C. and Rougeon, F., Purification of mouse immunoglobulin heavy chain messenger RNAs from total myeloma tumor RNA. Eur. J. Biochem., 107, 303–314 (1980).

Bank et al., U.S. Pat. No. 5,278,056.

Bates S E, Mickley L A, Chen Y N, Richert N, Rudick J, Biedler J L, et al. Expression of a drug resistance gene in human neuroblastoma cell lines: modulation by retinoic acid-induced differentiation. *Mol Cell Biol* 1989, 9, 4337–4344.

Carmichael, J., DeBraff, W. G. and Gazdar, A. F., Evaluation of tetrazolium-based semiautomated colorimetric assay: assessment of chemosensitivy, *Cancer Res.*, 47, 936–942 (1987).

Chaudhary, P. M., and Roninson, I. B. Activation of MDR1 (P-glycoprotein) gene expression in human cells by protein kinase C agonists. Oncol. Res., 4: 281–290, 1992.

Chaudhary, P. M., and Roninson, I. B. Induction of multi-drug resistance in human cells by transient exposure to different chemotherapeutic drugs. J. Natl. Cancer Inst., 85: 632–639, 1993.

Chen C-J, Chin J E, Ueda K, Clark D P, Pastan I, Gottesman M M, et al. Internal duplication and homology with bacterial transporter proteins in the mdr1 (P-glycoprotein) gene from multidrug-resistant human cells. *Cell* 1986, 47, 381–389.

Chin, K. V., Tanaka, S., Darlington, G., Pastan, I., and Gottesman, M. M. Heat shock and arsenite increase expression of the multidrug resistance (MDR1) gene in human renal carcinoma cells. J. Biol. Chem., 265: 221–226, 1990.

Chin K-V, Pastan I, Gottesman M M. Function and regulation of the human multidrug resistance gene. *Adv Cancer Res* 1993, 60, 157–180.

Chin K-V, Ueda K, Pastan I, Gottesman M M. Modulation of activity of the promoter of the human MDR1 gene by Ras and p53. *Science* 1992, 255, 459–462.

Choi K, Chen C-J, Kriegler M, Roninson I B. An altered pattern of cross-resistance in multidrug-resistant human cells results from spontaneous mutations in the mdr1 (P-glycoprotein) gene. *Cell* 1988, 53, 519–529.

Chu G, Hayakawa H, Berg P. Electroporation for the efficient transfection of mammalian cells with DNA. *Nucl Acids Res* 1987, 15, 1311–1326.

Culver et al., *Science*, Vol. 256, pp. 1550–1552 (1992).

Del Maestro, R. F., Lopez-Torres, M., McDonald, W. B., Stroude, E. C. and Vaithilingam, I. S., The effect of tumor necrosis factor-α on human malignant glial cells., *J. Neurosurg.*, 76, 652–659 (1992).

Diller L, Kassel J, Nelson C E, Gryka M A, Litwak G, Gebhardt M, et al. p53 functions as a cell cycle control protein in osteosarcomas. *Mol Cell Biol* 1990, 10, 5772–5781.

Dittmer D, Pati S, Zambetti G, Chu S, Teresky A K, Moore M, et al. Gain of function mutations in p53. *Nature Genet* 1993, 4, 42–46.

Evans, Ch. H. and Baker, P., Decreased P-glycoprotein expression in multidrug-sensitive and -resistant human myeloma cells induced by the cytokine leukoregulin, *Cancer Res.*, 52, 5893–5899 (1992).

Ferrandis, E. and Benard, J. Activation of the human mdr1 gene promoter in differentiated neuroblasts. Int. J. Cancer, 54: 987–991, 1993.

Flick, D. A. and Gifford, G. E., Comparison of in vitro cell cytotoxic assay for tumor necrosis factor, *J. Immunol. Methods*, 68, 167–175 (1984).

Frommel, T. O., Coon, J. S., Tsuruo, T., and Roninson, I. B. Variable effects of sodium butyrate on the expression and function of the MDR1 (P-glycoprotein) gene in colon carcinoma cell lines. Int. J. Cancer, 55: 297–302, 1993.

German, U. A., Pastan, I., and Gottesman, M. M. P-glycoproteins: mediators of multidrug resistance. Semin. Cell. Biol., 4: 63–76, 1993.

Goldstein L J, Galski H, Fojo A, Willingham M, Lai S-L, Gazdar A, et al. Expression of a multidrug resistance gene in human cancers. *J Natl Cancer Inst* 1989, 81, 116–124.

Hantzopoulos, P. A., Sullenger, B. A., Ungers, G. and Gilboa, E., Improved gene expression upon transfer of the adenosine desaminase minigene outside the transcriptional unit of a retroviral vector, *Proc. Natl. Aca. Sci. USA*, 86, 3519–3512 (1989).

Hennequin E, Delvincourt C, Pourny C, Jardillier J C. Expression of mdr1 gene in human breast primary tumors and metastases. *Breast Cancer Res Treatm* 1993, 26, 267–274.

Herzog, C. E., Tsokos, M., Bates, S. E., and Fojo, A. T. Increased mdr1/P-glycoprotein expression after treatment of human colon carcinoma cells with P-glycoprotein antagonists. J. Biol. Chem., 268: 2946–2952, 1993.

Hofsli, F. and Nissen-Meyer, J., Reversal of multidrug resistance by lipophilic drugs, *Cancer Res.*, 50, 3997–4002 (1990).

Hug. Richard G. Steight. Biochim. Biophys. Acta 1097: 1–17, 1991).

Iwahashi, T., Okochi, E., Ono, K., Sugawara, I., Tsuruo, T., and Mori, S. Establishment of multidrug resistant human colorectal carcinoma HCT-15 cell lines and their properties. Anticancer Res., 11: 1309–1312, 1991.

Jaeckle, K. A., Immunotherapy of malignant gliomas, *Seminars in Oncol.*, 21, 249–259 (1994).

Kellen, J. A., The reversal of multidrug resistance in cancer, *Anticancer Res.*, 13, 959–961 (1993).

Kioka, N., Yamano, Y., Komana, T., and Ueda, K. Heat-shock responsive elements in the induction of the multidrug resistance gene (MDR1). FEBS Lett., 13: 37–40, 1992.

Kohno, K., Sato, S., Takano, H., Matsuo, K., and Kuwano, M. The direct activation of human multidrug resistance gene (mdr1) by anticancer drugs. Biochem. Biophys. Res. Comm., 165: 1415–1421, 1989.

Kohno K, Sato S-I, Uchiumi T, Takano H, Kato S, Kuwano M. Tissue-specific enhancer of the human multidrug-resistance (MDR1) gene. *J Biol Chem* 1990, 265, 19690–19696.

Kohno, K., Tanimura, H., Sato, S., Nakayama, Y., Makino, Y., Wada, M., Fojo, A. T., and Kuwano, M. Cellular control of human multidrug resistance 1 (mdr-1) gene expression in absence and presence of gene amplification in human cancer cells. J. Biol. Chem., 269: 20503–20508, 1994.

Licht, T., Fiebig, H. H., Bross, K. J., Herrmann, F., Berger, D. P., Shoemaker, R., and Mertelsmann, R. Induction of multiple-drug resistance during anti-neoplastic chemotherapy in vitro. Int. J. Cancer, 49: 630–637, 1991.

Markowitz et al., *Virology*, 167, 400–406 (1988).

Matsumoto, T., Tani, E., Kaba, K., Shindo, H. and Miyata, H., Expression of P-glycoprotein in human glioma cell lines and surgical glioma specimens, *J. Neurosurg.*, 74, 460–466 (1991).

Mickley, L. A., Bates, S. E., Richert, N. D., Currier, S., Tanaka, S., Foss, F., Rosen, N., and Fojo, A. T. Modulation of the expression of a multidrug resistance gene (mdr1/P-glycoprotein) by differentiating agents. J. Biol. Chem., 264: 18031–18040, 1989.

Miller and Buttimore, *Molec. and Cell. Biol.*, Vol. 6, No. 8, pp. 2895–2902 (1986).

Miller, U.S. Pat. No. 4,861,719.

Miller, *Nature*, Vol. 357, pp. 455–460 (1992).

Morikawa, K., Walker, S. M., Nakajima, M., Pathak, S., Jessup J. M., and Fidler, I. J. Influence of organ environment on the growth, selection, and metastasis of human colon carcinoma cells in nude mice. Cancer Res., 48: 6863–6871, 1988.

Mousseau, M., Chauvin, Ch., Nissou, M.-F., Chaffanet, M., Plantaz, D., Pasquier, B., Schaerer, R., and Benabid, A., A study of the expression of four chemoresistance-related genes in human primary and metastatic brain tumours, *Eur. J. Cancer*, 29A, 753–759 (1993).

Nicolau Claude. Amelia Cudd. Critical reviews in therapeutic drug carrier systems 6: 239–271, CRC Press, Inc., 1989)

Noonan, K. F., Beck, C., Holzmayer, T. A., Chin, J. E., Wunder, J. S., Andrulis, I. L., Gazdar, A. F., Willman, C. K L., Griffith, B., von Hoff, D. D., and Roninson, I., B. Quantitative analysis of MDR1 (multidrug resistance) gene expression in human tumors by polymerase chain reaction. Proc. Natl. Acad. Sci. USA, 87: 7160–7164, 1990.

Nooter K, Herweijer H. Multidrug resistance (mdr) genes in human cancer. Br J. Cancer 1991, 63, 663–669.

Petros A. Hantzopoulos et al. Proc. Natl. Acad. Sci. USA 86: 3519–3523, 1989.

Pfeil, D., Bergmann, J., Fichtner, I., Stein, U., Hentschel, M., Rothe, I. and Goan, S. R., Multidrug resistance of murine leukemia cells characterization and correlation with cytochrome P=450 dependent activities, cytosolic calcium and cell cycle state, *Anticancer Res.*, 14, 571–576 (1994).

Pinedo H. M., et al. Cancer chemotherapy and biological response modifiers. Annual 12. Elsevier, Amsterdam-New York-Oxford, 1991).

Ram, A., Culver, K. W., Walbridge, S., Blaese, R. M and Oldfield, E. H., In situ retroviral-mediated gene transfer of the treatment of brain tumors in rats, *Cancer Res.*, 53, 83–88 (1993).

Regenass, V., Mueller, M., Curschellas, E. and Malter, A., Antitumour effects of tumour necrosis factor in combination with chemotherapeutic agents, *Int. J. Cancer*, 39, 266–274 (1987).

Roninson, I. B. The role of the MDR1 (P-glycoprotein) gene in multidrug resistance in vitro and in vivo. Biochem. Pharmacol., 43: 95–102, 1992.

Roninson I B. ed. Molecular and cellular biology of multidrug resistance in tumor cells. Plenum Press, New York and London, 1991.

Sambrook J, Fritsch E F, Maniatis T. eds. *Molecular cloning* 9.14–9.19, Cold Spring Harbor Laboratory Press, 1989.

Schiller, J. H., Storer, B. E., Witt, P. L., Alberti, D., Tombes, M. B., Arzoomanian, R., Proctor, R. A., McCarthy, D., Brown, R. R., VCoss, S. D., Remick, S. C., Grem, J. L., Borden, E. C. and Trump, D. L., Biological and clinical effects of intravenous tumor necrosis factor-alpha administered three times weekly, *Cancer Res.*, 51, 1651–1658 (1991).

Sparmann, G., Walther, W., Gunzburg, W. H., Uckert, W. and Salmons, B., Conditional expression of human TNF-α: a system for inducible cytotoxicity, *Int. J. Cancer*, 59, 103–107 (1994).

Stein, U., Walther, W., and Wunderlich, V. Point mutations in the mdr1 promoter region of human osteosarcomas are related with responsiveness to MDR relevant drugs. Eur. J. Cancer, 30A: 1541–1545, 1994.

Stein, U., Wunderlich, V., Haensch, W., and Schmidt-Peter, P. Expression of the mdr1 gene in bone and soft tissue sarcomas of adult patients. Eur. J. Cancer, 29A: 1979–1981, 1993.

Takatori, T., Ogura, M., and Tsuruo, T. Purification and characterization of NF-R2 that regulates the expression of the human multidrug resistance (MDR1) gene. Jpn. J. Cancer Res., 84: 298–303, 1993.

Tanimura, H., Kohno, K., Sato, S., Uchiumi, T., Miyazaki, M., Kobayashi M., and Kuwano, M. The human multidrug resistance 1 promoter has an element that responds to serum starvation. Biochem Biophys. Res. Comm., 183: 917–924, 1992.

Tracey, K. J. and Cerami, A., Tumor necrosis factor, other cytokines and disease, *Annu. Rev. Cell. Biol.*, 9, 317–343 (1993).

Uchiumi T, Kohno K, Tanimura H, Hidaka K, Asakuno K, Abe H, et al. Involvement of protein kinase in environmental stress-induced activation of human multidrug resistance 1 (MDR1) gene promoter. *FEBS Lett* 1993, 326, 11–16.

Uchiumi, T., Kohno, K., Tanimura, H., Matsuo, K, Sato, S, Uchida, Y., and Kuwano, M. Enhanced expression of the human multidrug resistance 1 gene in response to UV light irradiation. Cell Growth Differ., 4: 147–157, 1993.

Ueda K, Pastan I, Gottesman M M. Isolation and sequence of the promoter region of the human multidrug-resistance (P-glycoprotein) gene. *J Biol Chem* 1987, 262, 17432–17436.

Valenti, M., Cimoli, G., Parodi, S., Mariani, G. L., Venturini, M., Conte, P. F. and Russo, P., Potentiation of tumour necrosis factor-mediated cell killing by VP16 on human ovarian cancer cell lines. In vitro results and clinical implications, *Eur. J. Cancer*, 29A, 1157–1161 (1993).

W. Culver Kenneth et al. Science 256: 1550–1552, 1992;

Walther, W., Fichtner, I. and Uckert, W., Retrovirus-mediated gene transfer of tumour necrosis factor alpha into colon carcinoma cells generates a growth inhibition, *Anticancer Res.*, 13, 1565–1574 (1993).

Walther, W. and Stein, U., Influence of cytokines on mdr1 experssion in human colon carcinoma cell lines: increased cytotoxicity of MDR relevant drugs, *J. Cancer Res. Clin. Oncol.*, 120, 471–478 (1994).

Walther, W., Stein, U., and Eder, C. RNA analysis using miniprep RNA in RT-PCR. Bio Techniques, 17: 674–675, 1994.

Weinstein R S, Jakate S M, Dominguez J M, Lebovitz M D, Koukoulis G K, Kuszak J R, et al. Relationship of the expression of the multidrug resistance gene product (P-glycoprotein) in human colon carcinoma to local tumor aggressiveness and lymph node metastasis. Cancer Res 1991, 51, 2720–2726.

Wu, L., Smythe, A. M., Stinson, S. F., Mullendore, L. A., Monks, A., Scudiero, D. A., Paull, K. D., Koutsoukos, A. D., Rubinstein, L. V., Boyd, M. R., and Shoemaker, R. H. Multidrug-resistant phenotype of disease-oriented panels of human tumor cell lines used for anticancer drug screening. Cancer Res., 52: 3029–3034, 1992.

Yoshida, J., Wakabayashi, T., Mizuno, M., Sugita, K. and Yoshida, T., Clinical effect of intra-arterial tumor necrosis factor-α for malignant glioma, *J. Neurosurg.*, 77, 78–83 (1992).

Yu, J. S., Wei, M. X., Chiocca, E. A., Martuza R. L. and Tepper, R., Treatment of glioma by engineered interleukin-4 secreting cells, *Cancer Res.*, 53, 3125–3128 (1993).

Zastawny R L, Salvino R, Chen J, Benchimol S, Ling V. The core promoter region of the P-glycoprotein gene is sufficient to confer differential responsiveness to wild-type and mutant p53. *Oncogene* 1993, 8 1529–1535.

Zvi, Ram. Cancer Res. 53: 83–88, (1993).

The above references are herein incorporated by reference.

We claim:

1. An expression vector for the expression of a therapeutically relevant protein in mammalian cells, comprising the following elements, operably linked:
   a) an mdr1 promoter or functional part thereof which is inducible by cytostatic agents, and
   b) a gene coding for a therapeutically relevant protein.

2. The vector of claim 1 further comprising an mdr1 enhancer element.

3. The expression vector of claim 1, comprising a sequence selected from the group consisting of the following sequences of the mdr1 promoter and functional parts thereof:
   a) SEQ ID NO: 1
   b) SEQ ID NO: 2
   c) SEQ ID NO: 3, and
   d) SEQ ID NO: 4.

4. The expression vector of claim 1, comprising a sequence selected from the group consisting of the following mutated sequences of the mdr1 promoter and functional parts thereof:
   a) sequence: transition +103 T→C: SEQ ID NO: 5, and
   b) sequence: transversion +137 G→T: SEQ ID NO: 6.

5. The expression vector of claim 1, comprising the enhancer elements of the mdr1 gene containing the following sequence or functional parts thereof: SEQ ID NO: 7.

6. The expression vector of claim 1, wherein the therapeutically relevant protein is selected from the group consisting of an enzyme, a cytokine, an antibody and an antioncogene.

7. A method for causing expression of a therapeutic agent in a mammalian cell comprising:
   a) administering the vector of claim 1 to a cell; and
   b) administering an inducer of the mdr promoter to the cell of part a).

8. A method for testing the biological activity of a therapeutically relevant protein in a cell comprising:
   a) administering the vector of claim 1 to a cell;
   b) administering an inducer of the mdr promoter to the cell of part a), and
   c) testing for the biological activity of the protein.

9. The expression vector of claim 6, wherein the cytokine is selected from the group consisting of tumor necrosis factor alpha, interferon alpha, interferon gamma, interleukin-2 and interleukin-6.

* * * * *

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
       (A) LENGTH: 2090 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 1:

```
CAAGGACTGT TGAAAGTAGC AAGAGCTAGT TTGTTTTAGG TCCATCATGT TTTATATTCA      60
CACTTTCATG TCAGTGGAGC AAAGAAATGG AATACAATAT AATAGAATGG TAGAATCTTA     120
TTTTTAAAAT CTGTGTTATT CTGATCTTTA ACTTACTTAT ATCTTTGATA GAGATCTTTA     180
CCTGATGCTC AAGATTGTAG AAATAGTATA ATCAACATAA CAGTATAGCA CTGTATTTAT     240
ATCCTGCACT GTTTAGGGAG GGTTTAAGGC CATTCAAAAG GATACATAAA ATACAACAAG     300
ATTACATAAA TGAAAGGTGA GATAAAGCAA CAAAGCAAAA CAAAAGTGAA AACAGAGATC     360
ATAGGCACAA ATAAGATTAA AAACGCATGT AATGAAGATG AAAGCTTTTA CATTTACCCC     420
AGATGGACCA CAGGGTTGTT GTTAAGCCTT TAAACAGTGA ACAATGCTGT ACACTTGCAT     480
ATGCAATTAG AACATGTGGA AAAAATAGTG GCCTGTTAGA AGCCTAATTA ACAATTTGTG     540
AAAAAAAAAA AAAAAAAAAA AAAAAGAGG CCGAGCTGTA GCTCACGCCT GTAATCCCTG      600
CACTTTGGGA GGCCGAGGCG GGCGGATCAC GAGGTCAGGA GATCAAGACC ATCCTGGCTA     660
ACACAGTGAA ACCCAGTCTC TACGAAAAAT ACAAAAAATT AGCCGGGCGT GGTGGCGGGA     720
GCCTGTAGTC CCAGCTACCT GGGAGGCTGA GGCAGGAGAA TGGTGTGAAC CCGGGAGGCG     780
GAGCTTGCAG TGAGCCGAGA TCCTGCCACT GCACTCCAGC CTGGGCGACA AGCAAGCTC     840
CGTCTGCAAA AAAGAAAAAA GAAAGAAAAA CAAAAGAAAA CTTCATTGTA TTGTAAGGCC     900
AAGAACAAAA TATATCAAGA TAAGGAAAAT TTGTAGTCAA GAATAGAAAA AAATTATGGC     960
TTTGAAGTAT GAGTTATTTA AAGAAAGTGG AAACATCCTC AGACTATGCA GTAAAAAACA    1020
AAGTGATTTT CTTCTTCTAA ACTTATGCAA TAAACTGATA GGTAATATGT GAAAGTCATA    1080
GAATGTAGAC TAGAGGATAC AACAAACCTA TTTCCTCTAT GTTCATAAGA AGTAAGAAAA    1140
GCTCTGATGT GAGTTAGCAT TGCTTTACAA TTTTGAATTG TGCAGATTGC CAGTACTTTT    1200
CCTCAGTTTG AAGTAAATAG TGGACAGGAA AAAATATTAA ATGTTGGCAG TAAATATGGA    1260
AGGAAATTAC AACTAATGTA ATATGCTAAA ACATGCTATG TTTATTTTAC TAATTTGAAT    1320
TAAAATGTAA GAATTTAAAA TGCCCTGGAA AAACACGGGC ATTGATCTGA CGTCTGAAGT    1380
TTTAAAATAT TACACACTTT GAAATAGCAT TTGTACCTTG AAATACCTGT CTCTATATAT    1440
TTTTTAAAAC TTCCTTTTTC TTTCATTCCA TTTATCATCA AATAAAGGAT GAACAGATGT    1500
AACTCAGAAA CTGTCAAGCA TGCTGAAGAA AGACCACTGC AGAAAAATTT CTCCTAGCCT    1560
TTTCAAAGGT GTTAGGAAGC AGAAAGGTGA TACAGAATTG GAGAGGTCGG AGTTTTTGTA    1620
TTAACTGTAT TAAATGCGAA TCCCGAGAAA ATTTCCCTTA ACTACGTCCT GTAGTTATAT    1680
GGATATGAAG ACTTATGTGA ACTTTGAAAG ACGTGTCTAC ATAAGTTGAA ATGTCCCCAA    1740
TGATTCAGCT GATGCGCGTT TCTCTACTTG CCCTTTCTAG AGAGGTGCAA CGGAAGCCAG    1800
```

```
AACATTCCTC CTGGAAATTC AACCTGTTTC GCAGTTTCTC GAGGAATCAG CATTCAGTCA      1860

ATCCGGGCCG GGAGCAGTCA TCTGTGGTGA GGCTGATTGG CTGGGCAGGA ACAGCGCCGG      1920

GGCGTGGGCT GAGCACAGCG CTTCGCTCTC TTTGCCACAG GAAGCCTGAG CTCATTCGAG      1980

TAGCGGCTCT TCCAAGCTCA AGAAGCAGA GGCCGCTGTT CGTTTCCTTT AGGTCTTTCC       2040

ACTAAAGTCG GAGTATCTTC TTCCAAGATT TCACGTCTTG GTGGCCGTTC                 2090

(2) INFORMATION FOR SEQ ID NO: 2:

(i) SEQUENCE CHARACTERISTICS:
        (A) LENGTH: 1688 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

AGCTTTTACA TTTACCCCAG ATGGACCACA GGGTTGTTGT TAAGCCTTTA AACAGTGAAC        60

AATGCTGTAC ACTTGCATAT GCAATTAGAA CATGTGGAAA AATAGTGGC CTGTTAGAAG        120

CCTAATTAAC AATTTGTGAA AAAAAAAAAA AAAAAAAAA AAAAGAGGCC GAGCTGTAGC        180

TCACGCCTGT AATCCCTGCA CTTTGGGAGG CCGAGGCGGG CGGATCACGA GGTCAGGAGA      240

TCAAGACCAT CCTGGCTAAC ACAGTGAAAC CCAGTCTCTA CGAAAAATAC AAAAAATTAG      300

CCGGGCGTGG TGGCGGGAGC CTGTAGTCCC AGCTACCTGG GAGGCTGAGG CAGGAGAATG      360

GTGTGAACCC GGGAGGCGGA GCTTGCAGTG AGCCGAGATC CTGCCACTGC ACTCCAGCCT      420

GGGCGACAAA GCAAGCTCCG TCTGCAAAAA AGAAAAAAGA AAGAAAAACA AAAGAAAACT      480

TCATTGTATT GTAAGGCCAA GAACAAAATA TATCAAGATA AGGAAAATTT GTAGTCAAGA      540

ATAGAAAAAA ATTATGGCTT TGAAGTATGA GTTATTTAAA GAAAGTGGAA ACATCCTCAG      600

ACTATGCAGT AAAAACAAA GTGATTTTCT TCTTCTAAAC TTATGCAATA AACTGATAGG       660

TAATATGTGA AAGTCATAGA ATGTAGACTA GAGGATACAA CAAACCTATT TCCTCTATGT      720

TCATAAGAAG TAAGAAAAGC TCTGATGTGA GTTAGCATTG CTTTACAATT TTGAATTGTG      780

CAGATTGCCA GTACTTTTCC TCAGTTTGAA GTAAATAGTG GACAGGAAAA AATATTAAAT      840

GTTGGCAGTA AATATGGAAG GAAATTACAA CTAATGTAAT ATGCTAAAAC ATGCTATGTT      900

TATTTTACTA ATTTGAATTA AAATGTAAGA ATTTAAAATG CCCTGGAAAA ACACGGGCAT      960

TGATCTGACG TCTGAAGTTT TAAAATATTA CACACTTTGA AATAGCATTT GTACCTTGAA     1020

ATACCTGTCT CTATATATTT TTTAAAACTT CCTTTTTCTT TCATTCCATT TATCATCAAA     1080

TAAAGGATGA ACAGATGTAA CTCAGAAACT GTCAAGCATG CTGAAGAAAG ACCACTGCAG     1140

AAAAATTTCT CCTAGCCTTT TCAAAGGTGT TAGGAAGCAG AAAGGTGATA CAGAATTGGA     1200

GAGGTCGGAG TTTTTGTATT AACTGTATTA ATGCGAATC CCGAGAAAAT TTCCCTTAAC      1260

TACGTCCTGT AGTTATATGG ATATGAAGAC TTATGTGAAC TTTGAAAGAC GTGTCTACAT     1320

AAGTTGAAAT GTCCCCAATG ATTCAGCTGA TGCGCGTTTC TCTACTTGCC CTTTCTAGAG     1380

AGGTGCAACG GAAGCCAGAA CATTCCTCCT GGAAATTCAA CCTGTTTCGC AGTTTCTCGA     1440

GGAATCAGCA TTCAGTCAAT CCGGGCCGGG AGCAGTCATC TGTGGTGAGG CTGATTGGCT     1500

GGGCAGGAAC AGCGCCGGGG CGTGGGCTGA GCACAGCGCT TCGCTCTCTT TGCCACAGGA     1560

AGCCTGAGCT CATTCGAGTA GCGGCTCTTC CAAGCTCAAA GAAGCAGAGG CCGCTGTTCG     1620

TTTCCTTTAG GTCTTTCCAC TAAAGTCGGA GTATCTTCTT CCAAGATTTC ACGTCTTGGT     1680

GGCCGTTC                                                              1688
```

(2) INFORMATION FOR SEQ ID NO: 3:

(i) SEQUENCE CHARACTERISTICS:
        (A) LENGTH: 1318 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

```
GGGAGGCGGA GCTTGCAGTG AGCCGAGATC CTGCCACTGC ACTCCAGCCT GGGCGACAAA    60
GCAAGCTCCG TCTGCAAAAA AGAAAAAAGA AAGAAAAACA AAAGAAAACT TCATTGTATT   120
GTAAGGCCAA GAACAAAATA TATCAAGATA AGGAAAATTT GTAGTCAAGA ATAGAAAAAA   180
ATTATGGCTT TGAAGTATGA GTTATTTAAA GAAAGTGGAA ACATCCTCAG ACTATGCAGT   240
AAAAAACAAA GTGATTTTCT TCTTCTAAAC TTATGCAATA AACTGATAGG TAATATGTGA   300
AAGTCATAGA ATGTAGACTA GAGGATACAA CAAACCTATT TCCTCTATGT TCATAAGAAG   360
TAAGAAAAGC TCTGATGTGA GTTAGCATTG CTTTACAATT TTGAATTGTG CAGATTGCCA   420
GTACTTTTCC TCAGTTTGAA GTAAATAGTG GACAGGAAAA AATATTAAAT GTTGGCAGTA   480
AATATGGAAG GAAATTACAA CTAATGTAAT ATGCTAAAAC ATGCTATGTT TATTTTACTA   540
ATTTGAATTA AAATGTAAGA ATTTAAAATG CCCTGGAAAA ACACGGGCAT TGATCTGACG   600
TCTGAAGTTT TAAAATATTA CACACTTTGA AATAGCATTT GTACCTTGAA ATACCTGTCT   660
CTATATATTT TTTAAAACTT CCTTTTTCTT TCATTCCATT TATCATCAAA TAAAGGATGA   720
ACAGATGTAA CTCAGAAACT GTCAAGCATG CTGAAGAAAA ACCACTGCAG AAAAATTTCT   780
CCTAGCCTTT TCAAAGGTGT TAGGAAGCAG AAAGGTGATA CAGAATTGGA GAGGTCGGAG   840
TTTTTGTATT AACTGTATTA AATGCGAATC CCGAGAAAAT TTCCCTTAAC TACGTCCTGT   900
AGTTATATGG ATATGAAGAC TTATGTGAAC TTTGAAAGAC GTGTCTACAT AAGTTGAAAT   960
GTCCCCAATG ATTCAGCTGA TGCGCGTTTC TCTACTTGCC CTTTCTAGAG AGGTGCAACG  1020
GAAGCCAGAA CATTCCTCCT GGAAATTCAA CCTGTTTCGC AGTTTCTCGA GGAATCAGCA  1080
TTCAGTCAAT CCGGGCCGGG AGCAGTCATC TGTGGTGAGG CTGATTGGCT GGGCAGGAAC  1140
AGCGCCGGGG CGTGGGCTGA GCACAGCGCT TCGCTCTCTT TGCCACAGGA AGCCTGAGCT  1200
CATTCGAGTA GCGGCTCTTC CAAGCTCAAA GAAGCAGAGG CCGCTGTTCG TTTCCTTTAG  1260
GTCTTTCCAC TAAAGTCGGA GTATCTTCTT CCAAGATTTC ACGTCTTGGT GGCCGTTC    1318
```

(2) INFORMATION FOR SEQ ID NO: 4:

(i) SEQUENCE CHARACTERISTICS:
        (A) LENGTH: 568 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

```
CTGAAGAAAG ACCACTGCAG AAAAATTTCT CCTAGCCTTT TCAAAGGTGT TAGGAAGCAG    60
AAAGGTGATA CAGAATTGGA GAGGTCGGAG TTTTTGTATT AACTGTATTA AATGCGAATC   120
CCGAGAAAAT TTCCCTTAAC TACGTCCTGT AGTTATATGG ATATGAAGAC TTATGTGAAC   180
TTTGAAAGAC GTGTCTACAT AAGTTGAAAT GTCCCCAATG ATTCAGCTGA TGCGCGTTTC   240
TCTACTTGCC CTTTCTAGAG AGGTGCAACG GAAGCCAGAA CATTCCTCCT GGAAATTCAA   300
```

```
CCTGTTTCGC AGTTTCTCGA GGAATCAGCA TTCAGTCAAT CCGGGCCGGG AGCAGTCATC     360

TGTGGTGAGG CTGATTGGCT GGGCAGGAAC AGCGCCGGGG CGTGGGCTGA GCACAGCGCT     420

TCGCTCTCTT TGCCACAGGA AGCCTGAGCT CATTCGAGTA GCGGCTCTTC CAAGCTCAAA     480

GAAGCAGAGG CCGCTGTTCG TTTCCTTTAG GTCTTTCCAC TAAAGTCGGA GTATCTTCTT     540

CCAAGATTTC ACGTCTTGGT GGCCGTTC                                        568

(2) INFORMATION FOR SEQ ID NO: 5:

(i) SEQUENCE CHARACTERISTICS:
        (A) LENGTH: 351 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

CTTGCCCTTT CTAGAGAGGT GCAACGGAAG CCAGAACATT CCTCCTGGAA ATTCAACCTG      60

TTTCGCAGTT TCTCGAGGAA TCAGCATTCA GTCAATCCGG GCCGGGAGCA GTCATCTGTG     120

GTGAGGCTGA TTGGCTGGGC AGGAACAGCG CCGGGGCGTG GCTGAGCAC AGCGCTTCGC      180

TCTCTTTGCC ACAGGAAGCC TGAGCTCATT CGAGTAGCGG CTCTTCCAAG CTCAAAGAAG    240

CAGAGGCCGC TGTTCGTTTC CTTTAGGTCT TTCCACTAAA GTCGGAGTAT CTTCTTCCAA    300

GATTTCACGC CTTGGTGGCC GTTCCAAGGA GCGCGAGGTA GGGGCACGCA A             351

(2) INFORMATION FOR SEQ ID NO: 6:

(i) SEQUENCE CHARACTERISTICS:
        (A) LENGTH: 351 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

CTTGCCCTTT CTAGAGAGGT GCAACGGAAG CCAGAACATT CCTCCTGGAA ATTCAACCTG      60

TTTCGCAGTT TCTCGAGGAA TCAGCATTCA GTCAATCCGG GCCGGGAGCA GTCATCTGTG     120

GTGAGGCTGA TTGGCTGGGC AGGAACAGCG CCGGGGCGTG GCTGAGCAC AGCGCTTCGC      180

TCTCTTTGCC ACAGGAAGCC TGAGCTCATT CGAGTAGCGG CTCTTCCAAG CTCAAAGAAG    240

CAGAGGCCGC TGTTCGTTTC CTTTAGGTCT TTCCACTAAA GTCGGAGTAT CTTCTTCCAA    300

GATTTCACGC CTTGGTGGCC GTTCCAAGGA GCGCGAGGTA GGGTCACGCA A              351

(2) INFORMATION FOR SEQ ID NO: 7:

(i) SEQUENCE CHARACTERISTICS:
        (A) LENGTH: 694 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

CCCTTCTAAC CATGGCCAGT GCGTGATGAC TGCTTGGGAG AGGTTATCAT TGGTGTGTCC      60

CTTTGTCATT AGTAATCACG GGTGACTCCA CGGCAGAAGT CAGGTACACT GGGTCTGTCA    120

CTCACTCCGT GAGACAGCGG GCAGGTCCCC AAACTTCTCT GATCCTCTCT ATTTCCTGGT    180
```

```
TAGTCAATGG GAGATTAAAC CAAAACCAGA GGAAACATTG TGAGCAAACC AAGAGCACCT        240

CCTTGTCACC TCAGTTTATG CCGGGCCCTG GCTCCGAGCT ACTGAAACCG CAGCATGGGG        300

GAGTCTCCTG GGTGGGGTGC ACCATTGACA GGAGGCACTG TTTAAGGCCT CACAAAACGT        360

GGGCTTCCTC GCCCTGGGCC TGATGGTTCT TGAAGGCCAG GTTCCCTGCA AATCTGGCCT        420

CTCTTCCCAG TCAAGGCTGA AGTAAAGGGT GAGTTTCCAC TGCTTTTCAC AGTGGGTGTT        480

CTGGGGGCAA GGAGCTCCCG CGAAGAAGAG GAGGAAAAAC AAGCCTGGTC AGAGGGGCAC        540

AGACATGTGT CCCTCTGGCC TGGTACGTCG GGACTTCAGC AGCGTCTCAG ATATCACAAT        600

CGTCCGGGGC AGAAATTGTG ACGTGCCGCT GGGGTAGCTT GGCAGCTGTG GACACCGTTG        660

CTATGTAAGG CGGGAGGTGA GTCACTGTCT CCAA                                   694
```